US007803561B2

(12) United States Patent
Filardo et al.

(10) Patent No.: US 7,803,561 B2
(45) Date of Patent: Sep. 28, 2010

(54) GPR30 ESTROGEN RECEPTOR IN BREAST CANCERS

(75) Inventors: Edward J. Filardo, East Grenwich, RI (US); Edmond Sabo, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 102 days.

(21) Appl. No.: 11/703,347

(22) Filed: Feb. 6, 2007

(65) Prior Publication Data

US 2008/0131915 A1   Jun. 5, 2008

Related U.S. Application Data

(60) Provisional application No. 60/771,049, filed on Feb. 6, 2006, provisional application No. 60/856,101, filed on Nov. 1, 2006.

(51) Int. Cl.
  *G01N 33/53* (2006.01)
(52) U.S. Cl. .............................................. 435/7.2
(58) Field of Classification Search .................. None
  See application file for complete search history.

(56) References Cited

U.S. PATENT DOCUMENTS

| 4,676,980 | A | 6/1987 | Segal et al. ................ 424/85 |
| 4,816,567 | A | 3/1989 | Cabilly et al. .............. 530/387 |
| 4,946,778 | A | 8/1990 | Ladner et al. ............. 435/69.6 |
| 5,225,539 | A | 7/1993 | Winter ................... 530/387.3 |
| 5,545,806 | A | 8/1996 | Lonberg et al. ............... 800/2 |
| 5,545,807 | A | 8/1996 | Surani et al. ................. 800/2 |
| 5,569,825 | A | 10/1996 | Lonberg et al. ............... 800/2 |
| 5,625,126 | A | 4/1997 | Lonberg et al. ............... 800/2 |
| 5,633,425 | A | 5/1997 | Lonberg et al. ............... 800/2 |
| 5,661,016 | A | 8/1997 | Lonberg et al. ........... 435/172.3 |
| 5,916,771 | A | 6/1999 | Hori et al. ................ 435/69.6 |
| 5,939,598 | A | 8/1999 | Kucherlapati et al. ........ 800/25 |

FOREIGN PATENT DOCUMENTS

| EP | 0 308 936 A2 | 3/1989 |
| WO | WO 91/00360 | 1/1991 |
| WO | WO 92/20373 | 11/1992 |
| WO | WO 93/08829 | 5/1993 |
| WO | WO 94/02602 | 2/1994 |
| WO | WO 94/11026 | 5/1994 |
| WO | WO 96/27011 | 9/1996 |
| WO | WO 96/33735 | 10/1996 |
| WO | WO 96/34096 | 10/1996 |
| WO | WO 2005/099363 A2 | 10/2005 |
| WO | WO 2006/005468 | * 1/2006 |
| WO | WO 2006/005468 A1 | 1/2006 |

OTHER PUBLICATIONS

Filardo et al., "Distribution of GPR30, a Seven Membrane-Spanning Estrogen Receptor, in Primary Breast Cancer and its Association with Clinicopathologic Determinats of Tumor Progression", *Clin. Cancer Res.*, 12(21):6359-6366 (2006).
Filardo et al., "Association of GPR30, a Seven Membrance-Spanning Estrogen Receptor with Advanced (Metastatic) Breast Carcinoma and it's Correlation with Other Classical Prognostic Factors", Abstract #38, Modern Pathology, 19:12 (2006).
Bologa et al., "Virtual and Biomolecular Screening Converge on a Selective Agonist for GPR30", *Nat. Chem. Biol.*, 2(4):207-212 (2006).
Brennan et al., "Preparation of Bispecific Antibodies by Chemical Recombination of Monoclonal Immunoglobulin $G_1$ Fragments", *Science*, 229:81-83 (1985).
Brodeur et al., "Mouse-Human Myeloma Partners for the Production of Heterohybridomas", *Mono. Antib. Prod. Tech. Apps.*, pp. 51-63 (1987).
Caron et al., "Engineered Humanized Dimeric Forms of IgG Are More Effective Antibodies", *J. Exp. Med.*, 176:1191-1195 (1992).
Cole et al., "The EBV-Hybridoma Technique and Its Application to Human Lung Cancer", *Monoclonal Antibodies and Cancer Therapy*, pp. 77-96 (1985).
Cote et al., "Generation of Human Monoclonal Antibodies Reactive with Cellular Antigens", *Proc. Nat. Acad. Sci. USA*, 80:2026-2030 (1983).
Filardo, E.J., "Epidermal Growth Factor Receptor (EGFR) Transactivation by Estrogen Via the G-Protein-Coupled Receptor, GPR30: A Novel Signaling Pathway with Potential Significance for Breast Cancer", *J. Steroid Biochem. Mol. Biol.*, 80:231-238 (2002).
Filardo et al., "GPR30: A Seven-Transmembrane-Spanning Estrogen Receptor That Triggers EGF Release", *Trends Endocrinol. Metab.*, 16(8):362-367 (2005).
Fishwild et al., "High-Avidity Human IgGk Monoclonal Antibodies from a Novel Strain of Minilocus Transgenic Mice", *Nat. Biotech.* 14:845-851 (1996).
Goding et al., "Production of Monoclonal Antibodies", *Monoclonal Antibodies: Principles and Practice*, Chapter 3, pp. 59-103 (1986).
Gruber et al., "Efficient Tumor Cell Lysis Mediated by a Bispecific Single Chain Antibody Expressed in *Escherichia coli*[1]", *J. Immunol.*, 152(11):5368-5374 (1994).
Holliger et al., "'Diabodies': Small Bivalent and Bispecific Antibody Fragments", *Proc. Natl. Acad. Sci. USA*, 90:6444-6448 (1993).
Hoogenboom et al., "By-Passing Immunisation Human Antibodies from Synthetic Repertoires of Germline $V_H$ Gene Segments Rearranged in Vitro", *J. Mol. Biol.*, 227:381-388 (1992).
Hopp et al., "Prediction of Protein Antigenic Determinants from Amino Acid Sequences", *Proc. Nat. Acad. Sci. USA*, 78(6):3824-3828 (1981).
Huse et al., "Generation of a Large Combinatorial Library of the Immunoglobulin Repertoire in Phage Lambda", *Science*, 246:1275-1281 (1989).
Carmeci et al., "Identification of a gene (GPR30) with homology to the G-protein-coupled receptor superfamily associate with estrogen receptor expression in breast cancer", *Genomics*, 45:607-617 (1997).

(Continued)

*Primary Examiner*—Michael Pak
(74) *Attorney, Agent, or Firm*—Mintz, Levin, Cohn, Ferris, Glovsky and Popeo, P.C.; Ingrid A. Beattie, Esq.; Katherine J. Miller

(57) ABSTRACT

The invention provides methods of identifying metastatic disease as well as ligands such as antibodies that bind to GPR30. These antibodies are useful in the detection or treatment of endocrine tumors.

27 Claims, 15 Drawing Sheets

OTHER PUBLICATIONS

Feng et al., "Cloning of a novel member of the G protein-coupled receptor family related to peptide receptors", *Biochem. Biophys. Res. Comm.*, 231:651-654 (1997).

Filardo et al., "Estrogen-induced activation of erk-1 and erk-2 requires the G protein-coupled receptor homolog, GPR30, and occurs via trans-activation of the epidermal growth factor receptor through release of HB-EGF", *Mol. Endocrinol.*, 14(10):1649-1660 (2000).

Hewitt et al., "A new mediator for an old hormone?", *Science*, 307:1572-1573 (2005).

Kvingedal et al., "A novel putative G-protein-coupled receptor expressed in lung, heart and lymphoid tissue", *FEBS Lett.*, 407:59-62 (1997).

O'Dowd et al., "Discovery of three novel G-protein-coupled receptor genes", *Genomics*, 47:310-313 (1998).

Owman et al., "Cloning of human cDNA encoding a novel heptahelix receptor expressed in Burkitt's lymphoma and widely distributed in brain and peripheral tissues", *Biochem. Biophys. Res. Comm.*, 228:285-292 (1996).

Revankar et al., "Estrogen receptors in cell signaling", *Science*, 310:49-53 (2005).

Revankar et al., "A transmembrane intracellular estrogen receptor mediates rapid cell signaling", *Science*, 307:1625-1630 (2005).

Takada et al., "Cloning of cDNAs encoding G protein-coupled receptor expressed in human endothelial cells exposed to fluid shear stress", *Biochem. Biophys. Res. Comm.*, 240:737-741 (1997).

GenBank Accession No. CAG46541, Jun. 29, 2004.
GenBank Accession No. CAG46456, Jun. 29, 2004.
GenBank Accession No. NP_001026852, Oct. 18, 2005.
GenBank Accession No. NP_001496, Sep. 3, 2007.
GenBank Accession No. NP_084047, Oct. 7, 2007.
GenBank Accession No. XP_355659, Aug. 31, 2004.

Jones et al., "Replacing the Complementarity-Determining Regions in a Human Antibody with Those From a Mouse", *Nature*, 321:522-525 (1986).

Kohler et al., "Continuous Cultures of Fused Cells Secreting Antibody of Predefined Specificity", *Nature*, 256:495-497 (1975).

Kostelny et al., "Formation of a Bispecific Antibody by the Use of Leucine Zipper", *J. Immunol.*, 148(5):1547-1553 (1992).

Kozbor et al., "The Production of Monoclonal Antibodies From Human Lymphocytes",*Immunol. Today* 4(3):72-79 (1983).

Kozbor et al., "A Human Hybrid Myeloma for Production of Human Monoclonal Antibodies",*J. Immunol.*, 133(6):3001-3005 (1984).

Kyte et al., "A Simple Method for Displaying the Hydropathic Character of a Protein",*J. Mol. Biol.*, 157:105-132 (1982).

Lonberg et al., "Antigen-Specific Human Antibodies From Mice Comprising Four Distinct Genetic Modifications", *Nature*, 368:856-859 (1994).

Lonberg et al., "Human Antibodies From Transgenic Mice", *Intern. Rev. Immunol.*, 13:65-93 (1995).

Marks et al., "By-Passing Immunization: Building High Affinity Human Antibodies by Chain Shuffling", *Bio/Technol.*, 10:779-783 (1992).

Marks et al., "By-Passing Immunization Human Antibodies From V-Gene Libraries Displayed on Phage", *J. Mol. Biol.*, 222:581-597 (1991).

Milstein et al., "Hybrid Hybridomas and their Use in Immunohistochemistry",*Nature*, 305:537-540 (1983).

Morrison, S.L., "Success in Specification", *Nature*, 368:812-813 (1994).

Neuberger, M., "Generating High-Avidity Human Mabs in Mice", *Nat. Biotechnol.*, 14(7):826 (1996).

Presta, L.G., "Antibody Engineering", *Curr. Op. Struct. Biol.*, 2:593-596 (1992).

Riechmann et al., "Reshaping Human Antibodies for Therapy",*Nature*, 332: 323-327 (1988).

Munson et al., "Ligand: A Versatile Computerized Approach for Characterization of Ligand Binding Systems", *Anal. Biochem.*, 107:220-239 (1980).

Shalaby et al., "Development of Humanized Bispecific Antibodies Reactive with Cytotoxic Lymphocytes and Tumor Cells Overexpressing the *HER2* Protooncogene", *J. Exp. Med.*, 175:217-225 (1992).

Shopes, B., "A Genetically Engineered Human IgG Mutant with Enhanced Cytolytic Activity",*J. Immunol.*, 148(9):2918-2922 (1992).

Stevenson et al., "A Chimeric Antibody with Dual Fc Regions (bis FabFc) Prepared by Manipulations at the IgG Hinge", *Anti-Cancer Drug Design*, 3:219-230 (1989).

Suresh et al.,"Bispecific Monoclonal Antibodies from Hybrid Hybridomas", *Meth. Enzymol.*, 121:210-228 (1986).

Traunecker et al., "Bispecific Single Chain Molecules (Janusins) Target Cytotoxic Lymphocytes on HIV Infected Cells", *EMBO J.*, 10(12):3655-3659 (1991).

Tutt et al., "Trispecific F(ab')$_3$ Derivatives That Use Cooperative Signaling Via the TCR/CD3 Complex and CD2 to Activiate and Redirect Resting Cytotoxic T Cells", *J. Immunol.*, 147:60-69 (1991).

Verhoeyen et al., "Reshaping Human Antibodies: Grafting an Antilysozyme Activity",*Science*, 239:1534-1536 (1988).

Vitetta et al., "Redesigning Nature's Poisons to Create Anti-Tumor Reagents", *Science*, 238:1098-1104 (1987).

Wilkinson, D., "Immunochemical Techniques Inspire Development of New Antibody Purification Methods", *The Scientist*, 14(8): 25-28 (2000).

Wolff et al., "Monoclonal Antibody Homodimers: Enhanced Antitumor Activity in Nude Mice" ,*Cancer Res.*, 53:2560-2565 (1993).

\* cited by examiner

FIG. 3A  ER (+3)
FIG. 3B  PR (+3)
FIG. 3C  GPR30 (+1)
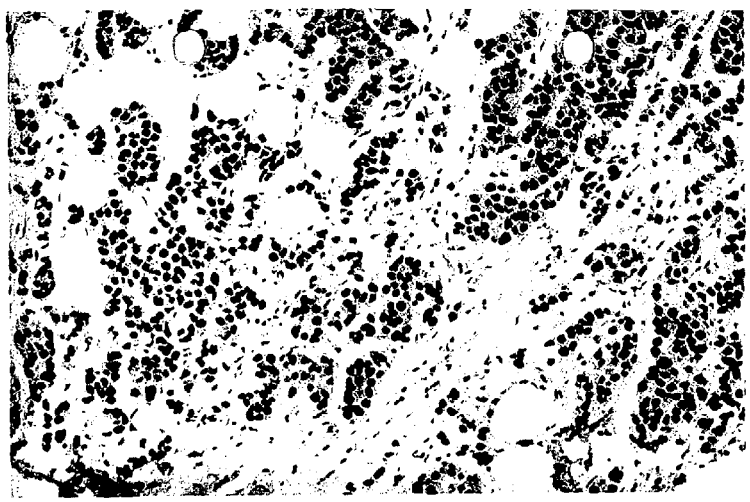
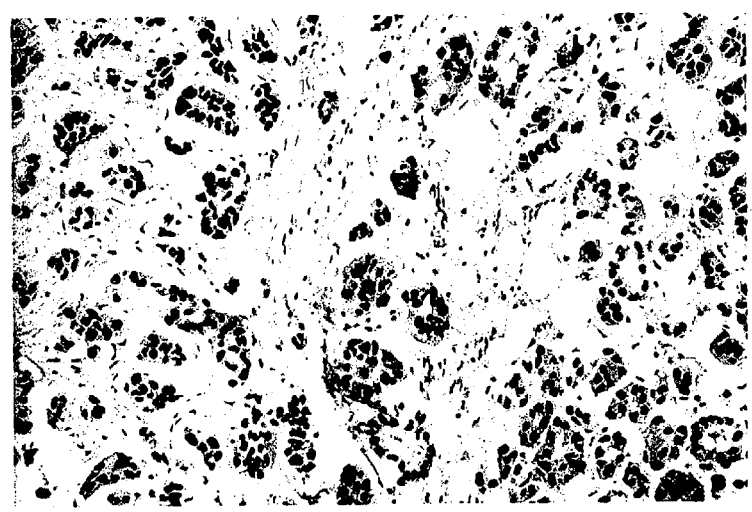
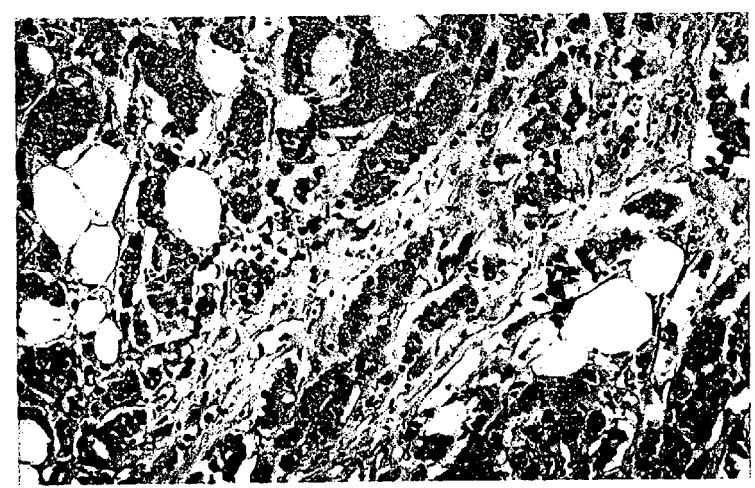

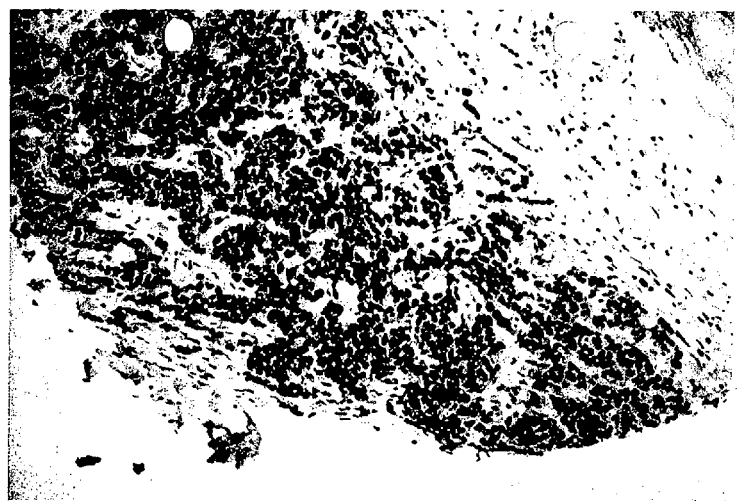
FIG. 3 D  ER (+3)
FIG. 3 E  PR (+2)
FIG. 3 F  GPR30 (+3)

GPR30 ESTROGEN RECEPTOR IN BREAST CANCERS

RELATED APPLICATIONS

This application claims priority to U.S. provisional patent application No. 60/771,049 filed on Feb. 6, 2006, and U.S. provisional patent application No. 60/856,101, filed on Nov. 1, 2006, the entire contents of which are hereby incorporated by reference.

STATEMENT AS TO FEDERALLY SPONSORED RESEARCH

This invention was made with U.S. Government support under Grant Number RR P20 RR017695 from the National Center for Research Resources, a component of National Institutes of Health. The government has certain rights in the invention.

FIELD OF THE INVENTION

The present invention relates to the field of cancer diagnostics.

BACKGROUND OF THE INVENTION

There are a number of predictive parameters employed clinically for determining the prognosis of patients with endocrine cancers, such as breast cancer. Such predictors of prognosis have a variety of different origins and are often used in different combinations to provide a better evaluation and result. One source of predictors is based on the anatomical extent of the cancer in the patient. The predictors thus include staging, tumor size, tumor margins, axillary node status, and tumor location within the breast. A second source of predictors is based on the tumor growth potential (aggressive or virulence). These predictors include invasive quality of the tumor, multi-centricity, histological types, histological grading, growth rate (cell kinetics), the presence or absence of steroid hormone receptors such as estrogen and progesterone receptors, as well as specific biological markers such as carcinoembryonic antigen (CEA) measurements, ferritin, C-reactive protein, acid glycoprotein, alkaline phosphatase, silayl transference and urinary hydroxyproline-creatinine ratios.

SUMMARY OF THE INVENTION

A method for predicting the occurrence of distant metastatic neoplastic disease in a subject diagnosed as comprising a primary tumor by detecting an increase in a GPR30 level in a tissue sample obtained from the primary tumor or a sample of a bodily fluid, e.g., blood, serum, lymphatic fluid, plasma, urine, saliva, semen, or breast milk, form a test subject. A distant metastasis from breast cancer is a tumor that occurs in an organ or tissue other than breast tissue. An increase in GPR30 protein or transcript compared to a normal control level or values indicates that the subject is suffering from or at risk of developing a malignant tumor at an anatomical site distant from the primary tumor. The tumor is an endocrine tumor such as breast cancer, ovarian cancer, colon cancer, prostate cancer and endometrial cancer. In one example, the method is useful to predict lymph node involvement such as axillary lymph node involvement. In another example, assessment of GPR30 and detection of an increase in GPR30 level is predictive of distant metastasis regardless of local lymph node involvement, i.e., the subject has been diagnosed with lymph node metastasis or a lack of such involvement.

GPR30 levels are measured by detecting GPR30 nucleic acids in a bodily tissue or fluid or by contacting the tissue or fluid with a GPR30-specific ligand, e.g, an antibody, and detecting binding of the ligand to the patient-derived sample of tissue, organ, or bodily fluid.

A method for predicting the presence of one or more tumorous foci in breast tissue of a subject diagnosed as comprising a primary tumor is carried out by detecting an increase in a GPR30 level in a tissue sample obtained from a primary tumor, tissue/organ from which the tumor was derived, or bodily fluid from the affected subject, e.g., a subject diagnosed as having a breast tumor or a lump that is diagnosed as being suspect of a malignant condition. An increase indicates that the subject is suffering from or at risk of developing one or more tumorous foci in an ipsilateral or contralateral breast relative to the primary tumor.

A method of prognosis for breast cancer patients includes the steps of detecting GPR30 in a sample of breast tissue or bodily fluid of the patient following excision of a primary tumor, and an elevation in the level of GPR30 compared to a normal control level or over time indicates recurrence of malignancy. A method for predicting survival time of a cancer patient is carried out by detecting GPR30 in a tissue biopsy in which an increase in GPR30 level is correlated with a decrease in survival time. The assay for prediction of survival of the individual or recurrence of a tumor is carried out before or after any treatment of the patient for the cancer.

The invention represents a major advance in the diagnosis and treatment of tumors of reproductive organs by providing an antibody that binds specifically to an GPR30 polypeptide. The antibody is preferably a monoclonal or fragments, homologs, analogs, and derivatives thereof. The antibody is useful to identify tumors that are characterized by an increase in estrogen receptor GPR30 compared to the level of expression in nontumor cells. Increased level of GPR30 in a sample of tumor tissue, e.g., resected tumor, biopsy sample, or archival tissue) indicates metastatic disease. Individuals identified as having GPR30-positive tumors regardless of their estrogen receptor alpha (ERα) or estrogen receptor beta (ERβ) expression status are treated differently compared to those with GPR30-negative tumors. This diagnostic information is critical to the determination of a clinical treatment regimen. For example, GPR30-positive patients are candidates for conventional chemotherapy and radiation to address metastases.

A significant advance in cancer therapy is the determination of adjuvant therapy for GPR30 positive tumors. In the absence of this diagnostic marker, it was difficult to determine which adjuvant therapy to administer to a given cancer patient. For example, anti-estrogen drugs such as tamoxifen and/or Faslodex (ICI 182,789) are administered to individuals with ER-positive tumors. Since these drugs activate GPR30, the administration of them is detrimental to the patient. The methods of the invention now permit identification of a subset of individuals with GPR30 positive tumors, thereby enabling physicians to appropriately tailor or refine adjuvant therapy, e.g, by selecting other anti-tumor agents such as aromatase inhibitors.

The invention also includes a pharmaceutical composition including GPR30 antibody and a pharmaceutically acceptable carrier or diluent. The invention is also directed to isolated antibodies that bind to an epitope on a polypeptide encoded by any of the nucleic acid molecules described herein.

As used herein, by "GPR30" is meant a polypeptide that is substantially identical to the naturally occurring GPR30 polypeptide (e.g., accession numbers CAG46541, CAG46456, NP_001026852, NP_001496, NP_084047, or XP_355659, the sequences of which are hereby incorporated by reference).

By a "GPR30 gene" is meant a nucleic acid that encodes a GPR30 protein.

By "GPR30 fusion gene" is meant a GPR30 promoter and/or all or part of a GPR30 coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and beta-galactosidase.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a GPR30 specific antibody. A purified antibody may be obtained, for example, by affinity chromatography using recombinantly-produced protein or conserved motif peptides and standard techniques.

By "specifically binds" is meant an antibody that recognizes and binds an antigen or antigenic domain such as an antigenic sequence in the Exodomain II of GPR30 (e.g., HERYYDIAVLC; SEQ ID NO; 1) but that does not substantially recognize and bind other non-antigen molecules in a sample, e.g., a biological sample, that naturally includes protein or domains of a target protein.

By "neutralizing antibodies" is meant antibodies that interfere with any of the biological activity of a GPR30 polypeptide. The neutralizing antibody may reduce GPR30 signaling activity by, preferably 50%, more preferably by 70%, and most preferably by 90% or more.

By "substantially identical," when referring to a protein or polypeptide, is meant a protein or polypeptide exhibiting at least 75%, but preferably 85%, more preferably 90%, most preferably 95%, or even 99% identity to a reference amino acid sequence. For proteins or polypeptides, the length of comparison sequences will generally be at least 20 amino acids, preferably at least 30 amino acids, more preferably at least 40 amino acids, and most preferably 50 amino acids or the full length protein or polypeptide. Nucleic acids that encode such "substantially identical" proteins or polypeptides constitute an example of "substantially identical" nucleic acids; it is recognized that the nucleic acids include any sequence, due to the degeneracy of the genetic code, that encodes those proteins or polypeptides. In addition, a "substantially identical" nucleic acid sequence also includes a polynucleotide that hybridizes to a reference nucleic acid molecule under high stringency conditions.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65 oC, or a buffer containing 48% formamide, 4.8×SSC, 0.2 M Tris-Cl, pH 7.6, 1×Denhardt's solution, 10% dextran sulfate, and 0.1% SDS, at a temperature of 42 oC. Other conditions for high stringency hybridization, such as for PCR, Northern, Southern, or in situ hybridization, DNA sequencing, etc., are well known by those skilled in the art of molecular biology. See, e.g., F. Ausubel et al., Current Protocols in Molecular Biology, John Wiley & Sons, New York, N.Y., 1998, hereby incorporated by reference.

By "substantially pure" is meant a nucleic acid, polypeptide, or other molecule that has been separated from the components that naturally accompany it. Typically, the polypeptide is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

The term "isolated DNA" is meant DNA that is free of the genes which, in the naturally occurring genome of the organism from which the given DNA is derived, flank the DNA. Thus, the term "isolated DNA" encompasses, for example, cDNA, cloned genomic DNA, and synthetic DNA.

By "an effective amount" is meant an amount of a compound, alone or in a combination, required to reduce or prevent the growth or invasiveness of a tumors of the reproductive system in a mammal. For example, the tumor is of an organ of the female reproductive system such a as a breast tumor or ovarian tumor. Alternatively, the tumor afflicts and organ of the male reproductive system such as the testes. The effective amount of active compound(s) varies depending upon the route of administration, age, body weight, and general health of the subject. Ultimately, the attending physician or veterinarian will decide the appropriate amount and dosage regimen.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof. The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20th edition, (ed. A. R. Gennaro), Mack Publishing Co., Easton, Pa., 2000.

Other features and advantages of the invention will be apparent from the following description of the preferred embodiments thereof, and from the claims. References cited are hereby incorporated by reference.

BRIEF DESCRIPTION OF THE DRAWINGS

FIGS. 3A-F are photomicrographs showing representative examples of invasive breast tumor tissue stained with GPR30, ER, and PR antibodies. Representative cases of archival, paraffin-embedded breast tumor tissue immunostained with ER, PR and GPR30: (FIGS. 3A-C) GPR30– invasive carcinoma; (FIGS. 3D-F) GPR30+ invasive carcinoma. All images are magnified 200×. Histochemistry scores for steroid hormone receptors are designated in each panel.

FIG. 9A shows cytochrome C reductase (NADPH) activities in the subcellular fractions, mem: plasma membrane, mem (s): plasma membrane fractions extracted with sucrose pad method, ms: microsomes; nu: nuclear; cyt: cytosol. mem (b): boiled plasma membrane. N=3. FIG. 9B shows specific [$^3$H] 17β-E2 binding to subcellular fractions. Dextran-coated charcoal was used to separate bound from free in the cytosolic fraction (#). N=3. FIG. 9C shows [$^{35}$S] GTPγS binding to the subcellular fractions after treatment with vehicle (Veh) or 100 nM 17β-E2, N=3, *: $P<0.05$ compared to corresponding untreated group. FIG. 9D shows results from Western blot analyses of subcellular fractions with human GPR30 antibodies, 15 μg of protein loaded/lane. N=2.

FIGS. 10A,D are photographs of electrophoretic gels, and FIGS. 10B,C are bar graphs showing the binding characteristics of subcellular fractions from SKBR3 cells. FIG. 10A shows results from a Western blot analyses of subcellular fractions using GPR30 peptide antibody, 40 μg of protein loaded/lane. N=2. FIG. 10B shows [3H] 17β-E2 binding to subcellular fractions. For key to symbols refer to the FIG. 6 legend. N=3. FIG. 10C shows [$^{35}$S] GTPγS binding to the subcellular fractions after treatment with 100 nM 17β-E2 or vehicle (Veh), N=3, *: $P<0.05$ compared to corresponding untreated group.

DETAILED DESCRIPTION

Figure 1:
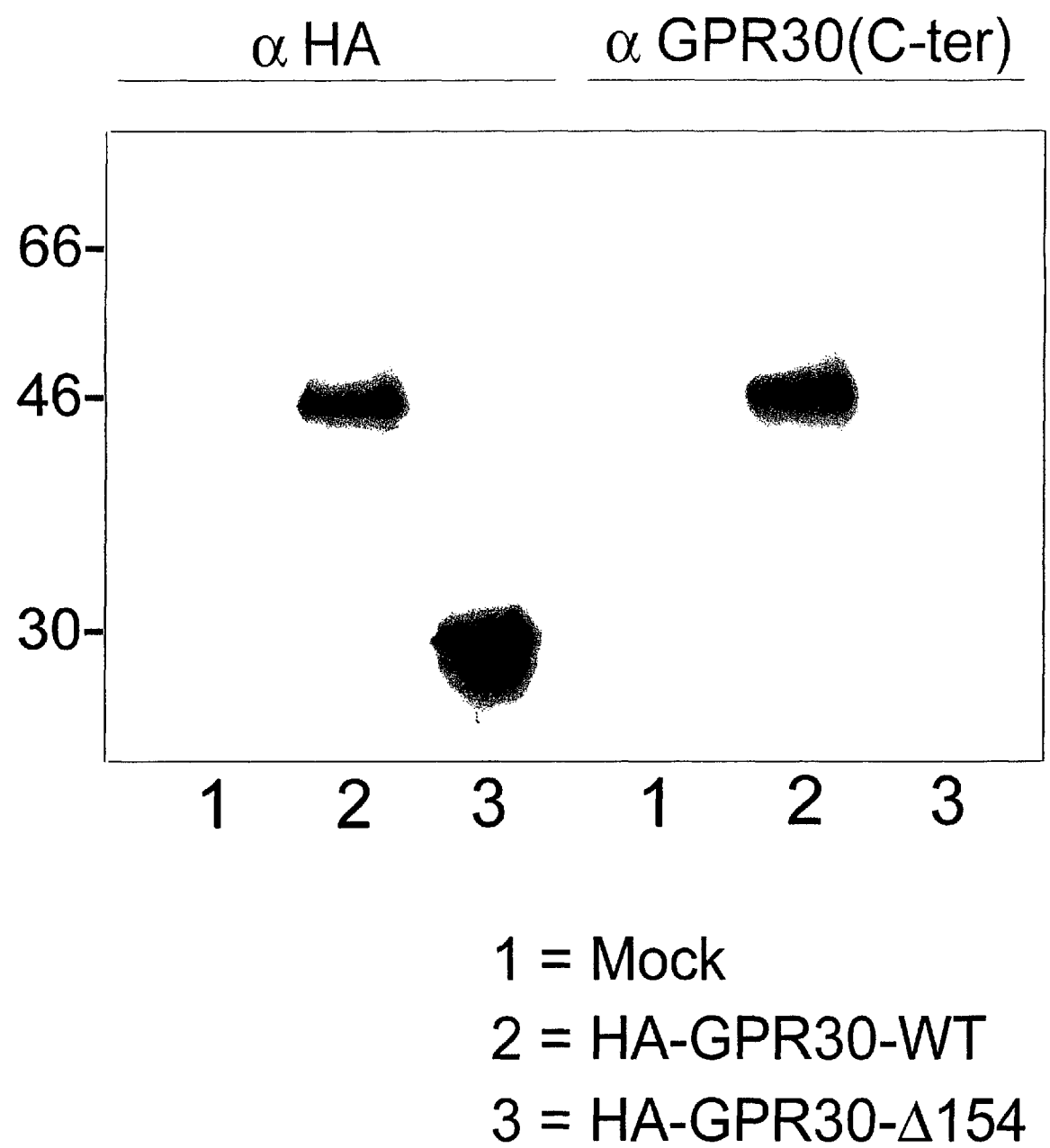
FIG. 1 is a photograph of an electrophoretic gel showing the specificity of GPR30 peptide antibodies. Total protein (25 µg) from HEK-293 cells transfected with: vector, HA-GPR30, or C-terminally truncated HA-GPR30 immunoblotted with anti-hemagluttinin (HA) or GPR30 C-TER peptide antibodies. Molecular mass standards are indicated at left (kDa).

Estrogen promotes the development and homeostasis of the mammary gland, and the growth of tumors that arise from this tissue. It is widely accepted that estrogen manifests its physiological and pathophysiological actions through its interaction with specific receptors. Estrogen receptor (ER) α, and its structural homologue ERβ, belong to the nuclear steroid hormone family and function indisputably as hormone-dependent transcription factors. Blockade of estrogen binding sites on the ER, has proven to be an effective means to inhibit the growth of breast tumors expressing ER, and this modality of treatment remains the standard endocrine therapy for ER-positive tumors. While there is general concordance between ER expression and responsiveness to ER antagonism, as indicated in greater disease-free survival at 5 year follow-up for postmenopausal patients with ER-positive tumors receiving tamoxifen, roughly one-in-four patients do not respond to tamoxifen therapy. A variety of explanations have been offered to account for nonresponsiveness to ER antagonism, including: i) intratumoral heterogeneity in ER expression, ii) evolution of mutant ERs with reduced affinity for ER antagonists, iii) drug resistance, iv) partial receptor antagonism, and v) the presence or absence of trans-acting factors that influence ER functionality. These interpretations have prompted strategies better designed to assess ER activity and have served as rationale for the discovery and use of new endocrine agents with more complete ER antagonist activity. In addition, comarkers that better predict ER functionality have been identified for the purpose of selecting patients that will respond favorably to ER antagonists. For example, coexpression of the progesterone receptor, PR, the gene transcription of which is directly regulated by ER-dependent gene transactivation has prognostic value for determining favorable responses to tamoxifen. In addition, more complete ER antagonists, such as fulvestrant, are being assessed in clinical trials for patients with primary and advanced breast cancer.

All the ERs are widely distributed. The ERα is found in endometrium, breast cancer cells, ovarian stroma cells and the hypothalamus, while ERβ is found in kidney, brain, bone, heart, lungs, intestinal mucosa, prostate, and endothelial cells. Different estrogenic compounds have different binding affinities for alpha and beta ERs. While 17-beta-estradiol binds equally well to both receptors, estrone and raloxifene bind preferentially to the alpha receptor, and estriol and genistein to the beta receptor. The concept of selective estrogen receptor modulators is based on the ability to selective activate (or block) one type of ER or to promote ER interactions with different proteins such as transcriptional co-activator or co-repressor proteins. Additionally, the different estrogen receptor combinations respond differently to various antagonists, and some compounds have partially agonistic and antagonistic effects, depending on the tissue. For example, Tamoxifen, is an ER agonist in bone and uterus, but antagonist in breast tissue, and is therefore used in breast cancer treatment.

The existence of alternative estrogen receptors, whose action is not blocked by ER antagonists, or possibly stimulated by ER antagonists, has also been offered as a possible explanation for tamoxifen nonresponsiveness. Studies in animal and cell models have long indicated that estrogen manifests physiological actions and biochemical effects inconsistent with its known genomic mechanism of action. For instance, estrogen induces EGF-like activity in female reproductive tissue and likewise activates biochemical signals typically associated with EGFRs. Estrogen also stimulates second messenger signaling characteristic of seven transmembrane-spanning receptors (7TMRs), including activation of calcium, cAMP and inositol triphosphate. The orphan 7TMR, GPR30, is linked to estrogen-mediated stimulation of adenylyl cyclase, release of heparan bound (HB)-EGF from the surface of breast cancer cells, and specific estrogen binding. GPR30 acts independently from ERα and ERβ, and triggers estrogen-dependent EGFR action. GPR30 plays an important role in breast cancer biology since it provides a mechanism by which estrogen promotes EGF-like effects. Breast tumors that lack ERs may remain estrogen responsive by employing GPR30. This concept is particularly intriguing for patients receiving endocrine therapy, since "partial" (tamoxifen) and "pure" (faslodex) ER antagonists behave similarly to estradiol, and are capable of triggering EGFR activation in breast cancer cells.

Seven-Transmembrane Receptors (7TMRs) in Rapid Estrogen Signaling

Figure 11:
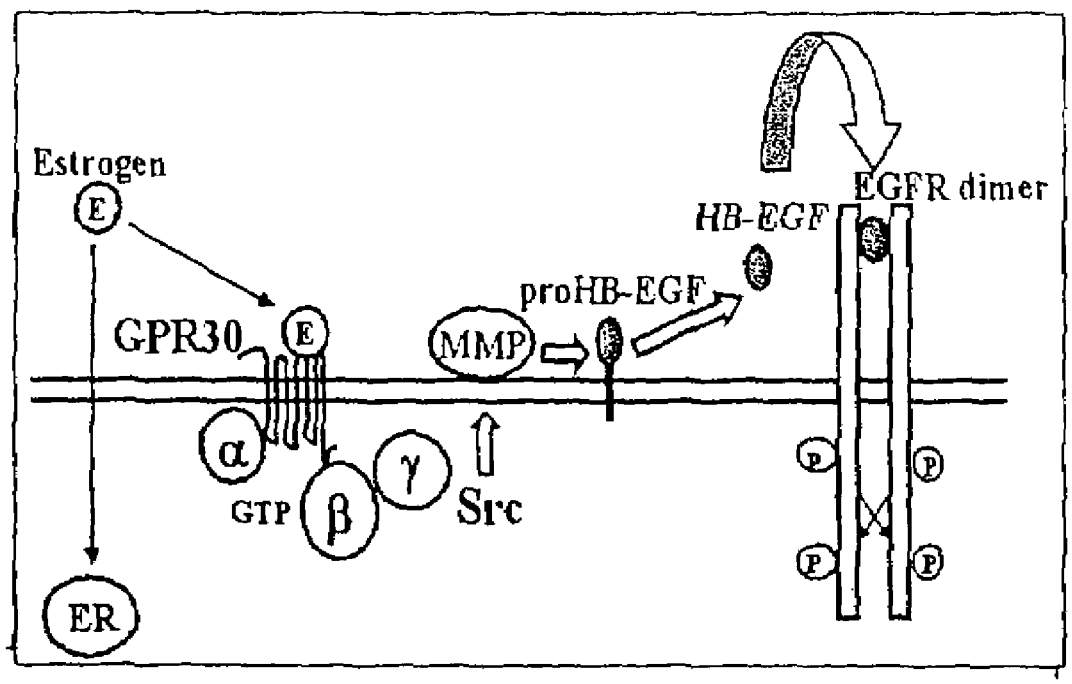
FIG. 11 is a diagram showing the mechanism by which GPR30 triggers release of EGF-related polypeptides. This cartoon illuminates the cellular signaling events that promote GPR30-mediated release of HB-EGF. GPR30 action occurs independently of the known estrogen receptors, ERα and ERβ and is also promoted by ER antagonists.

The observation that estrogen promotes rapid biochemical actions predates the first report describing the existence of specific binding activity for estrogen in extracts from rat female reproductive tissue. Early studies demonstrated that intrauterine administration of estrogen in rats resulted in a rapid rise in intracellular cAMP. However, the mechanism by which estrogen produced cAMP was largely ignored after the isolation of an estrogen receptor (ER) with structural characteristics of a hormone-inducible transcription factor. Subsequent experiments in vitro confirmed that estrogen generates cAMP as a result of its ability to stimulate adenylyl cyclase. Observations that estrogen also stimulates Ca2+, inositol triphosphate, and heterotrimeric G proteins indicated that a seven-transmembrane-spanning receptor (7TMR) might be implicated in rapid estrogen signaling. Rapid estrogen signaling was linked to the orphan receptor, GPR30 (FIG. 11). The amino acid sequence of GPR30 reveals a serpentine, heptahelical structure characteristic of 7TMRs.

Endocytic Fates of 7TMRs

Figure 12:
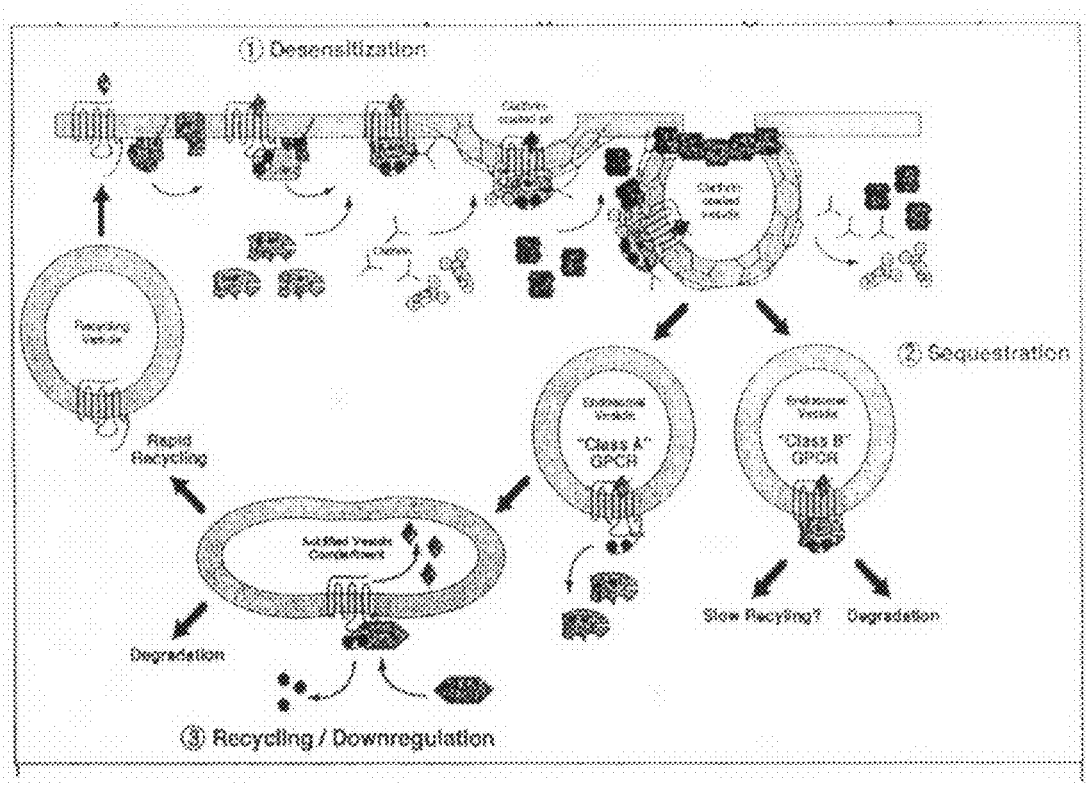
FIG. 12 is a diagram endocytic trafficking of 7TMRs. This cartoon illustrates molecular events that occur during receptor endocytosis, including: (1) receptor desensitization by β-arrestin and its subsequent (2) sequestration in clathrin-coated vesicles. Sequestered 7TMRs are sorted to endosomes that promote (3) receptor resensensitization "recycling" or receptor destruction by proteolysis "downregulation". In general, 7TMRs are divided into "class A" receptors that recycle rapidly and "class B" receptors that exhibit slow recycling kinetics.

7TMRs promote intracellular signals and biological responses as a result of changes in receptor activation and inactivation states. Binding of cognate ligand to 7TMRs, induces allosteric changes in their structure causing the 7TMR to function as a GDP/GTP exchange factor promoting the loading of GTP into the active site of the Gα-GTPase subunit and its subsequent release from the Gβγ subunit components of the receptor-associated Gαβγ heterotrimer. Both Gα- and Gβγ-proteins promote intracellular signaling events that ultimately provide feedback that attenuates 7TMR signaling and protects from receptor overstimulation. This process is initiated by receptor phosphorylation, and is often but not exclusively mediated by β-arrestins that bind phosphorylated 7TMRs resulting in the physical uncoupling of heterotrimeric G proteins from 7TMRs and their recruitment to endocytic machinery often via clathrin-coated pits. Once internalized, 7TMRs are sorted into two separate trafficking patterns (FIG. 12). Either they are dephosphorylated, resensitized and recycled back to the plasma membrane or they are marked for destruction in lysosomes, a process associated with ubiquitination of 7TMR, or associated proteins, such as β-arrestin. Based upon this interaction, receptors are divided into two classes. "Class A" receptors (β1-adrenergic receptors) form transient interactions with β-arrestin. These receptors do not require β-arrestin for internalization and recycle relatively rapidly. In contrast, "class B" receptors (angiotensin II and vasopressin receptors), bind β-arrestin more avidly and internalize together with it. These receptors recycle more slowly, which is reflected by their retention in endosomes or proteolysis in lysosomes.

Estrogen and EGF are important paracrine regulators of mammary gland development and homeostasis. Transactivation of EGFR by GPR30 has significance in breast cancer. The data described herein directly implicates GPR30 in breast tumor progression. These data positively associate GPR30 expression in primary tumors with increased tumor size, HER-2/neu, and metastases Antibody Specificity The present invention features antibodies or fragments thereof that specifically bind to GPR30. Such antibodies include monoclonal and polyclonal antibodies, that specifically bind to antigenic sequences within the GPR30 polypeptide (Accession Numbers CAG46541, CAG46456, NP_001026852, NP_001496, NP_084047, or XP_355659), which is described, for example, in Filardo and Thomas, Trends Endocrinol. Metab. 16: 362-7, 2005), and Filardo, J. Steroid Biochem. Mol. Biol. 80:231-8, 2002, which are hereby incorporated by reference. Epitope binding specificity of GPR30-specific monoclonal antibodies are defined by a sequence of 8, 10, 12, 15, 18, or 20 consecutive amino acids of a GPR30 protein sequence. For example, these epitopes correspond to consecutive residues in the sequence of GENBANK accession number CAG46541 (with the exception of the first 24 residues, which represent a signal sequence that is cleaved during post-translational processing).

Human GPR30 Amino Acid Sequence (SEQ ID NO:7 residues 1-24 correspond to signal peptide)

```
         10         20         30         40         50         60
MDVTSQARGV GLEMYPGTAQ PAAPNTTSPE LNLSHPLLGT ALANGTGELS EHQQYVIGLF 70         80         90        100        110        120
LSCLYTIFLF PIGFVGNILI LVVNISFREK MTIPDLYFIN LAVADLILVA DSLIEVFNLH 130        140        150        160        170        180
ERYYDIAVLC TFMSLFLQVN MYSSVFFLTW MSFDRYIALA RAMRCSLFRT KHHARLSCGL 190        200        210        220        230        240
IWMASVSATL VPFTAVHLQH TDEACFCFAD VREVQWLEVT LGFIVPFAII GLCYSLIVRV 250        260        270        280        290        300
LVRAHRHRGL RPRRQKALRM ILAVVLVFFV CWLPENVFIS VHLLQRTQPG AAPCKQSFRH 310        320        330        340        350        360
AHPLTGHIVN LAAFSNSCLN PLIYSFLGET FRDKLRLYIE QKTNLPALNR FCHAALKAVI

370
PDSTEQSDVR FSSAV;
```

| From | To | Length | Domain |
|---|---|---|---|
| 1 | 62 | 62 | Extracellular (Exo I) |
| 63 | 84 | 22 | TM1 |
| 85 | 96 | 12 | Cytoplasmic |
| 97 | 120 | 24 | TM2 |
| 121 | 132 | 12 | Extracellular (Exo II) |
| 133 | 153 | 21 | TM3 |
| 154 | 175 | 22 | Cytoplasmic |
| 176 | 194 | 19 | TM4 |
| 195 | 220 | 26 | Extracellular (Exo III) |
| 221 | 236 | 16 | TM5 |
| 237 | 259 | 23 | Cytoplasmic |
| 260 | 280 | 21 | TM6 |
| 281 | 306 | 26 | Extracellular (Exo IV) |
| 307 | 327 | 21 | TM7 |
| 328 | 375 | 48 | Cytoplasmic |

The antigenic sequences are located throughout the protein sequence, e.g., in the C-terminus, N-terminus, Exodomain II, or Exodomain IV of the GPR30 polypeptide. The antibody specifically binds an antigen in the following peptide sequences: HERYYDIAVLC (SEQ ID NO: 1; in Exodomain II), KQSFRHAHPLTGHIC (SEQ ID NO: 2; in Exodomain IV), CAVIPDSTEQSDVRFSSAV (SEQ ID NO: 3; in C-terminus), or MDVTSQARGVGLEMYPGTAQPAAC (SEQ ID NO: 4; in N-terminus). Preferred antibodies bind to domains that are extracellular or cytoplasmic, rather than embedded in the cell membrane (TM). For example, the antibodies are generated using peptides 15-25 residues in length (e.g., 18-mers, 19-mers, 20-mers, 21-mers) located in the Exo I, II, III, or IV domains (sequence coordinates described above) or in either of the cytoplasmic domains (sequence coordinates also described above).

The antibodies described herein are useful, for example, to detect the presence of a tumor cell in a biological sample (e.g., primary tissue biopsy, archival tissue (frozen or formalin-fixed), cultured cells or cell lines, or biological fluid (e.g., plasma or blood)) using any method known in the art including immunohistochemical methods or ELISA assays. The identification of cells expressing GPR30 identifies the biological sample as containing a tumor cell, such as a tumor cell of the reproductive system (e.g., breast tumor cell, ovarian tumor cell, or uterus tumor cell. Moreover, GPR30 monospecific antibodies are useful for screening for novel estrogen-based therapies for breast or ovarian cancer. Furthermore, the expression of GPR30 in a primary breast cancer predicts the risk or presence of distant metastases. The data indicate that the presence of GPR30 positive primary tumors have a higher likelihood of presenting with distant metastases compared to individuals with GPR30 negative primary tumors.

Prior to the invention, estrogen receptors, ERα and ERβ, were the primary clinicopathological variable used for determining adjuvant therapy for patients with primary and advanced breast cancer. Antagonists to such receptors (e.g., tamoxifen) however activate GPR30. Thus, GPR30 antibodies allow clinicians to refine the assignment of patients for appropriate adjuvant therapy since the identification of such tumors using the GPR30 antibodies described herein would identify patients in need of therapeutic strategies that differ from that based on ERα or β alone.

GPR30 as a Predictor of Breast Tumor Metastasis

Expression of GPR30 in primary breast tumors is strongly correlated with the presence of distant metastasis (p-value=0.014). Measurement of GPR30 in human breast tumors using GPR30 peptide antibodies, polyclonal or monoclonal, by immunohistochemical or biochemical analysis, is useful to determine whether a patient with primary breast cancer harbors metastatic seeds (visible or occult). The results of this measurement are used to determine decisions/options for the treatment of primary breast cancer. The data also has prognostive value in the detection of GPR30 levels, e.g., using GPR30 peptide-specific antibodies. Increased GPR30 expression in preneoplastic disease projects progression to frank neoplasia.

Identification of Patients for Adjuvant Therapy

GPR30, a 7 transmembrane (TM) G-protein coupled receptor (GPCR) is involved in estrogen-mediated cell signal transduction and estrogen binding. The GRP30 receptor acts independently from estrogen receptors, ERα and ERβ. About two-thirds of all breast cancers contain elevated levels of estrogen receptors compared to nontumor cells. These tumors are characterized as estrogen receptor positive (ER+). Patients with ER+ tumors are candidates for adjuvant hormone therapy. Antibodies and other ligands specific for GPR30 formulated as detectable probes are useful to identify cancer patients for hormone adjuvant therapy.

Adjuvant hormone therapy deprives cancer cells of the female hormone estrogen, which some endocrine-responsive cancer cells need to proliferate. In addition to surgery or radiation as a primary therapy, adjuvant hormone therapy with, e.g., an anti-hormone drug such as tamoxifen, inhibits proliferation of residual tumor cells, prevents the original cancer from returning and/or prevent the development of new cancers in the other locations or tissues. Identification of this subset of patients is critical to formulating an effective treatment regimen.

The GPR30-specific ligands described herein are also useful as tools for prognosis. ER+tumors tend to grow less aggressively than ER− tumors. Therefore, patients with ER+tumors (increased levels of GPR30 as determined using GPR-specific monoclonal antibodies described herein) have a better prognosis than those with lower levels of GPR30.

A tissue sample, e.g., a resected tumor or biopsy sample, is contacted with a GPR30-specific antibody and the level of GPR30 is determined and compared to a control value. The control value is a level of GPR30 that is associated with tumors of the reproductive system (e.g., breast cancer, ovarian cancer) that are not hormone receptor positive. An increase in the level of GPR30 compared to the control indicates that the patient from which the sample is obtained is a good candidate for hormone adjuvant therapy.

Diagnostic Reagents

The invention also provides a diagnostic reagent pack or kit containing one or more containers filled with one or more of the agents of the invention. Reagents, e.g., antibodies that specifically bind peptides containing an antigenic sequence of the Exodomain II of GPR30 (e.g., HERYYDIAVLC; SEQ ID NO: 1) for carrying out the diagnostic or prognostic assay may be packaged together as a kit. For example, the antibody is immobilized on a solid phase and packaged together with other reagents suitable for detecting the peptide-antibody complexes. For example, enzyme-conjugated reagents may be included. Antigenic peptides that bind specifically to the antibody may also be included as a standard or control reagent. For example, the solid phase component of the kit onto which an antibody is immobilized is an assay plate, an assay well, a nitrocellulose membrane, a bead, a dipstick, or a component of an elution column. The kit may also contain a second antibody or other detectable marker. The second antibody or marker is labeled, e.g., using a radioisotope, fluorochrome, or other means of detection. The pack or kit can be labeled with information regarding the sequence of execution (e.g., obtaining a biological sample, contacting with a peptide containing an antigenic sequence, and detecting the presence or absence of antibodies specific to the peptide in the biological sample), or the like. The pack or kit can be a single unit assay or it can be a plurality of unit assays. For the purpose of this invention, unit assays is intended to mean materials sufficient to perform only a single assay.

Identification of GPR30 Inhibitors

Therapeutic intervention for GPR30-overexpressing tumors includes administration of a GPR30 inhibitor to reduce or prevent metastasis.

Expression of GPR30 is required for rapid biochemical signaling events and subsequent cell biological effects measured in breast cancer cells. The monoclonal GPR30 peptide-specific antibody described herein is also useful to purify GPR30 protein for the purpose of determining the minimal binding sites necessary to support estrogen action as well as to identify inhibitors of estrogen/GPR30 binding. These mABs are useful in solid state assays for the purpose of measuring the activity of GPR30 for estrogen analogues, paralogues, homologues, other estrogen mimetics, xenoestrogens, anti estrogens, estrogen receptor antagonists, and selective estrogen response modifiers (SEMS). These assays employ traditional radioreceptor binding assays as well as binding assays for fluorescently labeled estrogen-like molecules. Furthermore, these antibodies are used for the measurement of receptor activity as measured by allosteric changes in receptor structure.

To screen for a GPR30 inhibitor, a cell expressing GPR30, e.g., COS cells that express recombinant GPR30-GFP, are contacted with one or more candidate compounds in the presence and absence of estrogen. A reduction in the level of estrogen binding in the presence of the candidate compound compared to the level in the absence of the candidate compound indicates that the candidate compound inhibits estrogen binding to GPR30. Similar binding studies are carried out using ERα and ERβ (e.g., using COS cells transfected with ERα-GFP or ERβ-GFP). Inhibition of binding in the GPR30 system but not the ERα/ERβ system indicates that the candidate compound specifically inhibits binding of estrogen to GPR30 (as compared to other estrogen receptors). 7TMRs undergo allosteric changes in receptor structure in response to binding agonist, antagonists and inverse agonists. Altered antibody binding therefore predicts a change in receptor structure and function. Similarly, candidate compounds are tested for their ability to inhibit or influence/alter the binding profile of a GPR30-specific antibody, e.g., an antibody with a binding specificity for a particular epitope of GPR30 (SEQ ID NO: 1, 2, 3, or 4). Those candidate compounds that inhibit estrogen binding and/or binding of a GPR30-specific antibody are further tested for their effect on intracellular calcium mobilization and PI-3 kinase (PI3K) activation. Binding assays and signal transductions assays such as calcium mobilization and PI3K measurements are well known in the art, e.g., Bologa et al., 2006, Nat. Chem. Biol 2:207-212. A reduction in the level of calcium mobilization and/or PI3K activation in the cell compared to the level of mobilization observed with estrogen indicates that the candidate compound inhibits GPR30 activity in a cell and is useful to inhibit GPR30-mediated tumor growth and progression and/or GPR30-mediated metastasis.

Another strategy involves using two GPR30 antibodies to measure GPR30 activity by resonance energy transfer such as Fluorescence Resonance Energy Transfer (FRET) or Bioluminescence Resonance Energy Transfer (BRET). For example, a FRET assay is carried out as follows. Each antibody is coupled to a different fluorochrome. One fluorochrome emits at a higher energy than the excitation energy of the second fluorochrome. These antibody-fluorochrome conjugates are then applied to freshly isolated tumor specimens (not fixed) and exposed to a light source that activates fluorochrome 1 but not 2. Fluorochrome 2 absorbs light reemitted from fluorochrome 1. The amount of energy transferred is a function of distance. This assay measures a change in the distance between the site occupied by the first antibody and the second antibody, and thus indicates that GPR30 has changed its shape and thus its activity. Evidence of an allosteric change is useful for assessing how active GPR30 is in a tumor specimen, and thereby influence decisions regarding therapy.

For example, mABs are used to tag two different structural regions of the extracellular face of the receptor, e.g., exo II and exo IV. mAB to exo II is tagged with a fluor that absorbs in the blue range and reemits in the green range. Exo IV mAB is tagged with a fluor that absorbs light in the green range and reemits in the red range. In a static state, blue light absorbed by exo II mAB is reabsorbed as green light by the exo IV mAB and reemited as red light. The efficiency by which the energy is transferred (Fluorescence Resonance Energy Transfer) is a function of the distance between the two fluors. If the receptor binds its ligand (17β-estradiol), the receptor undergoes a conformational change that alters the distance between Exo II and Exo IV and hence indicates that the ligand induced a change in receptor conformation.

To screen for compounds that reduce GPR30 activity, GPR30-specific antibody/fluorochrome binding is carried out in the presence and absence of a candidate compound. Detection of an allosteric change in the presence of the compound compared to its shape (as detected by FRET or BRET) in the absence of the compound indicates that the compound alters the function of GPR30.

GPR30 Antibodies

Disclosed herein are antibodies to GPR30 proteins, or fragments of GPR30 proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Preferably, the monoclonal antibody is IgG or IgM isotype. Furthermore, in humans, the light chain may be a kappa chain or a lambda chain. Reference herein to antibodies includes a reference to all such classes, subclasses and types of human antibody species.

An isolated GPR30-related protein serves as an antigen, or a portion or fragment thereof, and is used as an immunogen to generate antibodies that immunospecifically bind the antigen using standard techniques for polyclonal and monoclonal antibody preparation. The fill-length protein or, antigenic peptide fragments of the antigen are used as immunogens. An antigenic peptide fragment comprises at least 6 amino acid residues of the amino acid sequence of the full length protein, such as an amino acid sequence shown in SEQ ID NO: 1, SEQ ID NO: 2, SEQ ID NO: 3, or SEQ ID NO: 4, and encompasses an epitope thereof such that an antibody raised against the peptide forms a specific immune complex with the full length protein or with any fragment that contains the epitope. Preferably, the antigenic peptide contains at least 8, 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of a GPR30-related protein that is located on the surface of the protein, e.g., a hydrophilic region. A hydrophobicity analysis of the human GPR30-related protein sequence will indicate which regions of a GPR30-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, Proc. Nat. Acad. Sci. USA 78: 3824-3828, 1991; Kyte and Doolittle J. Mol. Biol. 157: 105-142, 1982, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256: 495, 1975. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro. The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001, 1984; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220, 1980. Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal. The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522-525, 1986; Riechmann et al., Nature, 332: 323-327, 1988; Verhoeyen et al., Science, 239:1534-1536, 1988), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596, 1992).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96). In addition, human antibodies can also be produced using additional techniques, including phage display libraries (Hoogenboom and Winter, J. Mol. Biol., 227: 381, 1991; Marks et al., J. Mol. Biol., 222:581, 1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. Bio/Technology 10, 779-783, 1992; Lonberg et al. Nature 368 856-859, 1994; Morrison, Nature 368, 812-13, 1994; Fishwild et al, Nature Biotechnology 14, 845-51, 1996; Neuberger Nature Biotechnology 14, 826 1996; and Lonberg and Huszar Intern. Rev. Immunol. 13: 65-93, 1995.

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305: 537-539, 1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 *EMBO J.*, 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210, 1986.

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers. Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared using chemical linkage. Brennan et al. (Science 229:81, 1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers (Kostelny et al., J. Immunol. 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (Proc. Natl. Acad. Sci. USA 90:6444-6448, 1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/20373; EP 0308936). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). Homodimeric antibodies with enhanced anti-tumor activity can also be prepared using heterobifunctional cross-linkers as described in Wolff et al. Cancer Research, 53: 2560-2565 (1993). Alternatively, an antibody can be engineered that has dual Fc regions and can thereby have enhanced complement lysis and ADCC capabilities. See Stevenson et al., Anti-Cancer Drug Design, 3: 219-230 (1989).

Immunoconjugates

Immunoconjugates containing an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate) are also within the scope of the invention.

Cytotoxic agents or enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The role of GPR30 as an independent factor in human breast cancer was studied, and the relative tissue distribution of GPR30, ER and PR was assessed in intraductal and invasive ductal carcinoma, and correlated with other known histopathological markers of disease.

GPR30 Expression in Breast Cancer

The seven transmembrane receptor, GPR30, is linked to estrogen binding and release of HB-EGF from breast cancer cells. Studies were carried out to evaluate the significance of GPR30 in human breast cancer by comparing its relationship to steroid hormone receptor expression and tumor progression variables. GPR30 expression was determined by immunohistochemical analysis of a tumor collection comprised of 361 breast carcinomas obtained at first diagnosis (321 invasive and 40 intraductal tumors). Biopsies from 12 reduction mammoplasties served as controls. The distribution pattern of GPR30, ER, PR was correlated with clinicopathological variables obtained at diagnosis. GPR30, ER and PR were positive in all 12 normal controls. In contrast, variation in GPR30 expression was measured in breast tumors, where 62% (199/321) of invasive tumors and 42% (17/40) of intraductal tumors were positive. Codistribution of ER and GPR30 was measured in 43% (139/321) of invasive breast tumors, while both receptors were lacking (ER-GPR30-) in 19% (61/321) of the tumors analyzed, indicating a significant association between ER and GPR30 ($p<0.05$). Coexpression of PR and ER did not influence GPR30 expression, yet coexpression of GPR30 and ER was linked to PR positivity. Unlike ER, which varied inversely with HER-2/neu and tumor size, GPR30 positively associated with HER-2/neu and tumor size. In addition, GPR30 showed a positive association with metastasis ($p=0.014$, OR=1.9). These data indicate that GPR30 and ER exhibited distinct patterns of association with breast tumor progression variables, including HER-2/neu, tumor size and metastatic disease and indicate that GPR30 and ER have independent influence on estrogen responsiveness in breast carcinoma.

The following materials and methods were used to generate the data described herein.

Tissue specimens. Archival paraffin-embedded; formalin-fixed biopsy specimens of normal breast tissue were obtained from patients who underwent reduction mammoplasty. Breast tumor microarrays, consisting of 40 intraductal breast tumors and 333 invasive ductal carcinoma, were provided by the National Cancer Institute Cooperative Breast Cancer Tissue Resource. All tumor samples present in the NCI microarrays were collected at first diagnosis (prior to adjuvant or neoadjuvant therapy). The NCI microarrays were used for studies measuring the association of novel markers with breast tumor progression since they are comprised of tumors collected from several institutes and reflect reported frequencies of breast tumor progression variables.

Immunohistochemical analysis. GPR30 antibodies were generated in New Zealand white rabbits against a C-TER peptide (CAVIPDSTEQSDVRFSSAV; SEQ ID NO:3) comprising the carboxyl terminal 18 amino acid residues from the deduced amino acid sequence of human GPR30. Sera from immunized rabbits were affinity-purified on peptide columns before use. For GPR30 staining, formalin-fixed tissues were deparaffinized by heating slides to 60° C. for one hour followed by three consecutive extractions in Citrisolv (Fisher Scientific, Pittsburgh, Pa.). Tissues were then washed in ethanol, rehydrated and heated at 95° C. for 20 minutes in 0.1 M sodium citrate, pH 6.0. Endogenous peroxidase activity was quenched in 3% $H_2O_2$ and nonspecific binding was blocked using bovine serum albumin. Slides were exposed to GPR30 peptide antibodies for 2 hours at ambient temperature and then washed three times in tris-buffered saline containing 0.05% Tween 20. Tissue-associated rabbit antibodies were detected using a dextran-coated polymer containing horse-radish-peroxidase-conjugated goat anti-rabbit IgG (Envision-plus™) and diaminobenezidine as a substrate (Dako Cytomation, Carpinteria, Calif.). Nuclei were counterstained using Mayer's modified hematoxylin (PolyScientific, Bay Shore, N.Y.).

ER, PR and Her-2/neu staining scores were determined by NCI-selected pathologists and were provided in the blind key that accompanied the CBCTR microarrays after submission of GPR30 results. For the purpose of showing representative examples of ER and PR staining in the tumor microarray sets evaluated, ER and PR were immunostained on a Dako Autostainer using the Envision-plus™ detection system.

Evaluation of the immunostaining pattern for GPR30. Two observers using a semiquantitative scoring system microscopically evaluated intensity, extent and subcellular distribution of GPR30. Scores were applied as follows: score 0: negative staining in all cells, score 1+: weakly positive or focally positive staining in less than 10% of the cells, score 2+: moderately positive staining covering 10% to 50% of the cells, and score 3+: strongly positive staining, including more than 50% of the cells. For statistical analysis as well as to reduce intraobserver variability, the immunohistochemical scores were further grouped in two categories: negative or weakly positive (0 and 1+) and moderately to strongly positive (+2 and +3). Patient data were derived from a blind key provided by the NCI after reporting GPR30 scores.

Statistical analysis. Associations between steroid receptor expression categories and tumor stage were evaluated using the Chi square test or the Fisher's exact test, as needed. Two parametric groups were compared using the student T test for independent samples. Comparison between two non-parametric (ordinal) groups was done using the Mann-Whitney U test. Two-tailed p values of 0.05 or less were considered to be statistically significant.

GPR30-Specific Antibodies

Specificity of the GPR30 C-TER peptide antibodies for GPR30 protein was tested by immunoblot analysis of whole cell lysates prepared from HEK-293 cells transfected with epitope-tagged recombinant GPR30 (FIG. 1). Affinity-purified GPR30 antibodies detect a single band with an apparent molecular weight of 44 kDa in detergent lysates prepared from HEK-293 cells transfected with recombinant GPR30 containing an amino-terminal HA tag. This 44 kDa GPR30-reactive species was also detected upon reprobing the filter with HA-specific antibodies. However, this band was not detected in mock-transfected HEK-293 cells probed with either GPR30 or HA antibodies. In addition, GPR30 C-TER antibodies did not detect a truncated GPR30 polypeptide (30 kDa) expressed in HEK-293 cells that lacks its carboxyl terminus but retains the amino terminal HA epitope. These data indicate that GPR30 C-TER peptide antibodies specifically detect the carboxyl terminus of GPR30 protein.

Staining Pattern of GPR30 in Normal and Breast Cancer Tissue

Figure 2:
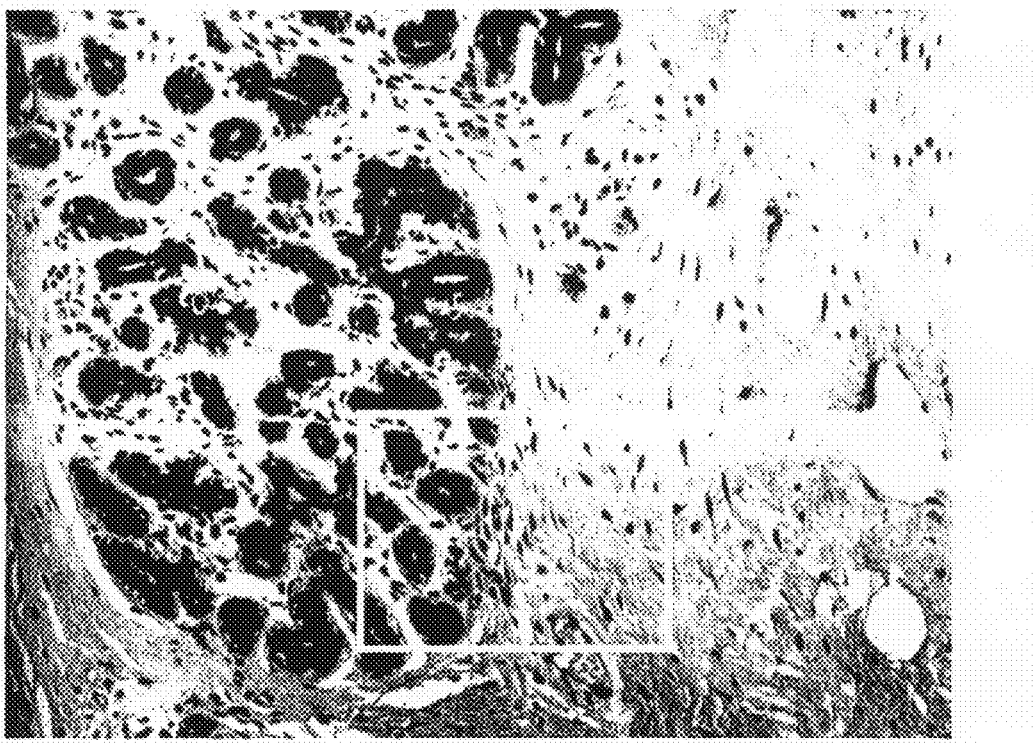
FIGS. 2A and 2B are photomicrographs of normal breast tissue immunostained with GPR30 peptide antibodies. Reductive mammoplasty tissue was immunostained with GPR30 peptide antibodies. Image magnified 200×.
Figure 2:
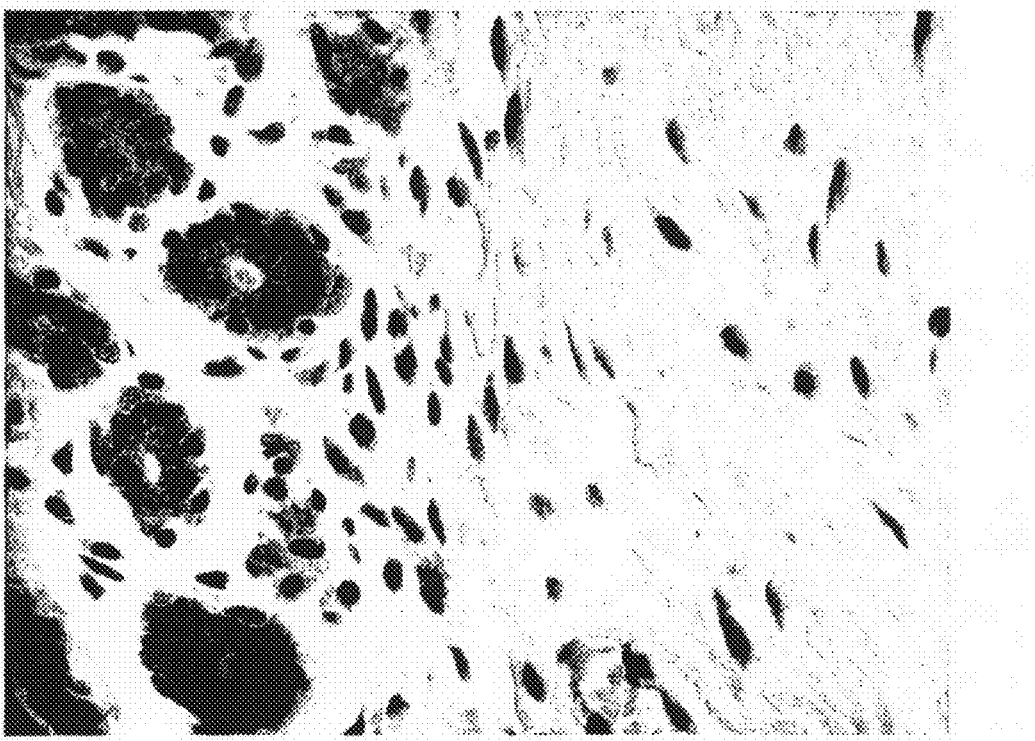

Affinity-purified GPR30 peptide antibodies were used to stain archival, paraffin-embedded breast specimens. The predominant staining pattern of GPR30 was cytoplasmic in both normal (FIGS. 2A-B) and ductal carcinoma (FIGS. 3A-F). This subcellular localization pattern is typical of seven-transmembrane receptors in tissue and has been observed in GPR30 in cultured breast cancer cell lines. The specificity of the cytoplasmic GPR30 immunoreactivity pattern of peptide antibodies was confirmed by demonstrating specific inhibition in immunoabsorption experiments comparing immune versus control peptide. In normal breast tissue, ductal and lobular epithelium, myoepithelial and stromal cells reacted strongly with GPR30 peptide antibodies, displaying a cytoplasmic staining pattern (FIGS. 2A-B). No nuclear staining was observed in these cells. Vascular endothelium and smooth muscle did not exhibit detectable staining. Similar staining patterns were observed in each of the twelve mammoplasties that were evaluated for the intensity and extent of GPR30 staining. The same cell types were positive with ER and PR antibodies. However, ER and PR immunoreactivity was exclusively confined to the nucleus with no detectable staining apparent within the plasma membrane or cytoplasm. No significant differences were measured in ER or PR expression within this normal breast tissue series. ER, PR and GPR30 expression each varied within breast tumor specimens as described below.

Distribution of GPR30, ER and PR in Breast Tumor Tissue

To compare the distribution of GPR30 and ER, PR steroid hormone receptors, adjacent serial sections collected from three hundred and sixty-one cases of intraductal or invasive ductal carcinoma were analyzed by immunohistochemistry (FIGS. 3A-F). Unlike normal breast, tumor tissue demonstrated variation in GPR30 staining with immunopositivity ranging from 0 to +3 (FIGS. 3C,F; Table I). Biopsies exhibiting little or no GPR30 (+1 or 0) were considered negative, while tumor specimens that scored moderately or strongly (+2 or +3) for GPR30 were categorized as positive. As observed in normal tissue, all GPR30 positive tumor biopsies exhibited a cytoplasmic staining pattern. No detectable cytoplasmic or plasma membrane staining was observed for ER (FIGS. 3A,D) or PR (FIGS. 3B,E). Of forty DCIS cases, 42% were GPR30 positive (Table I), while 63% and 45% of the DCIS specimens were positive for ER or PR, respectively. Among the 321 cases of invasive ductal carcinoma analyzed, 40% were positive for PR (Table I). Approximately, two-thirds (62%) of the breast tumors that were evaluated demonstrated ER-positivity, with a similar percentage of tumors expressing the alternative estrogen receptor, GPR30 (Table I).

TABLE I

Distribution of GPR30 and steroid hormone receptors in intraductal and invasive ductal carcinoma of the breast[4].

| Tissue | PR+ | ER+ | GPR30+ |
| --- | --- | --- | --- |
| DCIS | 18/40 (45%) | 25/40 (63%) | 17/40 (42%) |
| Invasive | 129/321 (40%) | 200/321 (62%) | 199/321 (62%) |

[4]Steroid hormone receptors were scored from 40 cases of DCIS and 321 cases of invasive ductal carcinoma.

GPR30 was found to be strongly associated with ER ($p<0.05$), but not with PR ($p=0.48$) (Tables II and III). Forty-three percent of all invasive tumors (139/321) expressed ER and GPR30 (Table II). Among the remaining categories, the following expression pattern of these two estrogen receptor types was measured: ER+GPR30−; 61/321 (19%); ER−GPR30+; 60/321 (19%); and ER−GPR30−; 61/321 (19%). While these data indicate a significant association between ER and GPR30, their expression in tumors is not interdependent since one-half of ER-tumors (60/121) are positive for GPR30. This result implies that these tumors may remain estrogen responsive despite the fact that they lack detectable ER (Table II). However, PR expression was approximately twice as common in tumors that coexpressed GPR30 and ER compared to tumors that produced ER but not GPR30 (Table III; 68% versus 32%). No significant differences were observed in the GPR30 expression levels between ER+PR+ and ER+PR breast tumors [73/107 (68%) and 66/93 (71%), respectively]. This observation is significant in light of the fact that PR-positivity has been used as a means to predict responsiveness to estrogen therapy.

The PR is an ER-regulated gene product (i.e., ER transcriptional regulatory sites are present in the PR promoter). When ER is active (capable of binding estrogen), PR expression is expected to increase. Measurement of ER+PR+ indicates that the ER is functional, and a patient should respond to ER antagonism. Conversely, ER+ but PR− is an indication that a nonfunctional ER is produced, i.e., it cannot upregulate PR. The prognosis for patients with the latter profile is that they would not respond well to ER antagonism. Such patients would be candidates for treatment with aromatase inhibitors, if they are diagnoses as responsive to estrogen by another mechanism such as GPR30.

TABLE II

Coexpression of GPR30 with ER or PR.

| Steroid hormone receptors | GPR30-positive | GPR30-negative | p-value |
|---|---|---|---|
| ER (n) | | | <0.05 |
| positive | 139/321 (43%) | 61/321 (19%) | |
| negative | 60/321 (19%) | 61/121 (19%) | |
| PR (n) | | | 0.48 |
| positive | 83/321 (26%) | 46/321 (14%) | |
| negative | 116/321 (36%) | 76/321 (24%) | |

TABLE III

Coexpression of ER, PR, and GPR30.

| Steroid hormone receptors | GPR30-positive | GPR30-negative |
|---|---|---|
| ER+ PR+ | 73/107 (68%) | 34/107 (32%) |
| ER+ PR− | 66/93 (71%) | 27/93 (29%) |
| ER− PR+ | 10/22 (45%) | 12/22 (55%) |
| ER− PR− | 50/99 (52%) | 49/99 (48%) |

Association of GPR30 with HER-2/neu

Via GPR30, 17β-estradiol triggers release of HB-EGF from the surface of cultured breast cancer cells and induces tyrosyl phosphorylation of EGFRs. For this reason, the relationship between GPR30 and HER-2/neu may be significant in breast cancer (Table IV). Within the 321 breast tumors included in this study, HER-2/neu data was available for 143 cases. GPR30 positive tumors presented higher HER-2/Neu expression scores than GPR30 negative tumors (p=0.038, see Table IV). These findings are in contrast with the inverse association observed between ER and HER-2/neu (p=0.003, OR=0.1). These data confirm in vitro data regarding the capacity of GPR30 to promote EGFR-dependent action. Moreover, the fact that ER and GPR30 demonstrate distinct patterns of association with HER-2/neu supports a mechanism by which each of these estrogen receptors exert distinct biological effects on breast tumors.

TABLE IV

Association between GPR30 expression and factors in breast carcinoma.

| Variable | GPR30-positive | GPR30-negative | p value |
|---|---|---|---|
| Age (mean ± SEM) | 60.2 ± 1.0 | 59 ± 1.2 | 0.32 |
| Tumor grade (n) | | | |
| High | 44 | 32 | 0.60 |
| Intermediate | 114 | 69 | |
| Low | 41 | 21 | |
| Tumor size (n) | | | |
| >2 cm | 103 | 49 | 0.05 |
| ≦2 cm | 96 | 73 | |
| [A]Lymph node involvement (n) | | | |
| 0 | 67 | 49 | 0.06 |
| 1-3 | 44 | 73 | |
| ≧4 | 42 | 24 | |
| Distant metastases (n) | | | |
| Present | 76 | 30 | 0.014 |
| Absent | 123 | 92 | |
| [B]HER-2/neu score (n) | | | |
| +3 | 11 | 1 | 0.038 |
| +2 | 7 | 3 | |
| +1 | 23 | 5 | |
| 0 | 61 | 32 | |

[A]Lymph nodes were not excised in 65 cases.
[B]HER-2/neu data was available for 143 cases.

Association of GPR30 with Other Clinicopathological Parameters

The relation between GPR30 and additional clinicopathological variables such as ER status, PR status, HER-2/neu status, tumor grade, tumor size and lymph node (LN) involvement was evaluated (Table IV). Axillary (armpit) lymph nodes (approximately 24 nodes/side) start at the chest wall and spread into the armpit. In addition to ER status, LN invasion is used to stratify treatment. ER+patients with no lymph node involvement generally receive ER antagonists. Patients with 1-3 LN are treated more aggressively, and patients with more than 4 LN are treated most aggressively.

No significant association was observed between GPR30 and patient age (p=0.32). Unlike ER and PR, which demonstrate a significantly inverse relationship with tumor grade (p<0.0001 in both cases), GPR30 was not significantly associated with grade (p=0.60). As observed in this study, an inverse relationship was measured between ER and tumor size (p=0.045; OR=0.62). In contrast, GPR30 expression varied directly with tumor size (p=0.05, OR=1.6). While GPR30 expression was found equally in both large (>2 cm) and small (<2 cm) invasive breast tumors, lack of GPR30 expression was almost twice as common in small invasive breast cancers (Table IV), indicating that GPR30 promotes tumor growth. Tumor size is a well-known predictor of lymph node metastasis. However, GPR30 demonstrated only marginal significance with regards to predicting lymph node invasion (p=0.06), when arranging the number of lymph nodes involved into clinically relevant treatment groups (Table IV). Interestingly though, GPR30 expression at the primary tumor site was strongly associated with the development of distant (extra-mammary) metastases (p=0.014, OR=1.9). Among the 215 patients that showed no evidence of distant metastases, similar proportions of patients expressing (55%) or lacking (45%) GPR30 in their tumor were observed (Table V). However, of the 106 patients presenting with distant metastases at first diagnosis, GPR30 expression was detected almost twice as commonly in the primary invasive tumor component (72% versus 28% of patients with metastases).

TABLE V

Association between clinicopathological variables and metastatic disease.

| Variable | nonmetastatic, n = 215 | metastatic, n = 106 | p value |
|---|---|---|---|
| Age (mean ± SEM) | 58 ± 0.9 | 62 ± 1.3 | 0.008 |
| GPR30 (n) | | | |
| positive | 123 | 76 | 0.014 |
| negative | 92 | 30 | |
| ER (n) | | | |
| positive | 127 | 73 | 0.08 |
| negative | 88 | 33 | |
| PR (n) | | | |
| positive | 88 | 41 | 0.7 |
| negative | 127 | 65 | |
| [A]HER-2/neu score (n) | | | |
| +3 | 4 | 8 | <0.0001 |
| +2 | 2 | 8 | |
| +1 | 18 | 10 | |
| 0 | 71 | 22 | |
| Tumor grade (n) | | | |
| high | 54 | 22 | 0.17 |
| intermediate | 115 | 68 | |
| low | 46 | 16 | |
| Tumor size (cm ± SEM) | 2.1 + 0.1 | 2.6 ± 0.1 | 0.003 |
| Lymph node involvement | | | |
| n = >4 | 43 | 23 | <0.0001 |
| n = 1-3 | 64 | 15 | |
| n = 0 | 108 | 3 | |

[A]HER-2/neu data was available for 143 cases.

Prior to the invention, tumor size, lymph nodes invasion and HER-2/neu expression were the best-documented predictors of metastatic breast carcinoma. Similar findings are shown in Table V, thus indicating that the tumors analyzed were representative of those included in other studies. Furthermore, the results described herein indicate that GPR30 is a significant predictor of tumor size and metastases, but not of lymph node invasion, despite the fact that GPR30 is associated with HER-2/neu overexpression. This relationship is distinct from that observed between ER and tumor size, nodal invasion and the occurrence of distant metastases, in which the absence of ER is strongly associated with HER-2/neu, nodal tumor involvement and the presence of distant metastases.

GPR30 levels are a reliable indicator of lymph node as well as distant metastasis. An elevated level of GPR30 indicates metastasis to other tissues or organs such as liver or lung in addition to metastasis into the lymphatic system, e.g., to the spleen and/or remote lymph nodes (other than axillary nodes). Relative levels also provide and indication of severity of the disease, and an increase over time indicates an adverse prognosis. An increase in GPR30 level also indicates (1) the presence as well as the extent of local invasion in the ipsilateral breast; (2) the presence of more than one tumorous focus, in the same breast in a location that is distinct from the primary tumor; (3) the presence of one or more primary tumorous focus/foci in the contralateral breast (i.e. not metastases but additional primary tumorous foci in the same breast or in the contralateral breast); (4) the survival time of breast cancer patients, with or without invasion, with or without lymph node or distant metastases; and (5) the occurrence of local or distant recurrence as well as the recurrence times in the breast cancer patients, with or without invasion, with or without lymph node or distant metastases. Thus, measuring GPR30 levels provides critical prognostic information regarding survival, recurrence, lymphovascular invasion, local ipsilateral and/or contralateral occurrence of in situ or of invasive tumor. Elevated levels predict the existence of additional primary tumors, i.e., tumorous foci (invasive or in situ) within the same breast (ipsilateral) or within the controlateral breast, the relative number of lymph nodes involved by the tumor, the relative number of metastatic foci in any organ, and the tumor size. The GPR30 level is directly correlated with greater number of tumor-positive lymph nodes and/or tumorous foci in breast tissue as well as greater tumor mass. This information is pertinent to all types of breast cancer including invasive breast cancer as well as in situ tumors (e.g., ductal carcinoma in situ, lobular carcinoma in situ).

The data presented here support the mechanism that ER and GPR30 are structurally distinct estrogen receptors that have separate biological influences on the growth and progression of breast cancer.

Distribution of GPR30, a Seven-Membrane-Spanning Estrogen Receptor in Primary Breast Cancer and its Association with Clinicopathological Determinants of Tumor Progression.

Endocrine therapy is particularly successful in breast cancer patients, and ER expression status in breast carcinomas is one of the most important variables to be considered for the management of primary and advanced breast cancer patients. However, a complete concordance between tamoxifen responsiveness and ER expression does not exist, and whether this is associated with errors in tumor sampling, intratumoral heterogeneity, and absence of cofactors that support ER functionality is unclear. Alternatively, receptors other than the known estrogen receptors, ERγ and ERβ, may be important for the growth and survival of breast cancer cells. This hypothesis is largely supported by studies which shown that "pure" ER antagonists, such as ICI 182, 780 (faslodex) have agonistic effects in cultured cells and that some estrogen effects are maintained in double ERKO mice. Support for alternative estrogen receptors comes from experiments in rodents showing the EGF-like effects of estrogen. Namely, that estrogen induces mitogenic responses in female reproductive tissues that can be ablated with neutralizing antibodies against EGF. Moreover, in cultured cells, estrogen promotes rapid biochemical signals typically associated with membrane receptors that either couple to heterotrimeric G proteins or harbor intrinsic tyrosine kinase activity.

GPR30 is an alternative receptor for estrogen that is structurally distinct from ERα and ERβ. This receptor belongs to the seven-transmembrane (7™) spanning receptor superfamily. Autonomy of GPR30 from ERα or ERβ is reflected by two measures. First, GPR30 expression is associated with estrogen binding activity and estrogen-mediated intracellular signaling in breast cancer cell lines that do not express ERα or ERβ. Secondly, while ER antagonists compete for GPR30-dependent estrogen binding sites, they act similarly to estrogen in their capacity to elicit estrogen-mediated signals. The biological role of GPR30 in breast cancer was elucidated by comparing the distribution of this alternative estrogen and the steroid hormone receptors, ER and PR, in human breast tumors.

With regard to subcellular localization, GPR30 displayed a predominately cytoplasmic staining pattern in normal and tumor breast tissue (FIGS. 2A-B). This result is consistent data demonstrating a similar subcellular distribution pattern by immunocytochemistry in human SKBR3 breast cancer cells. Numerous other studies have demonstrated a similar cytoplasmic location for other 7TMRs, including neurotransmitter receptors and cytokine receptors, and this phenotype is likely due to slow egress to the plasma membrane during biogenesis as well as receptor reuptake. By immunohistochemical analysis using peptide antibodies, GPR30 protein was detected in normal breast tissue. While some tumors demonstrated slightly more GPR30 expression than in normal tissue, gross overexpression of GPR30 in breast tumor tissue was not observed (FIGS. 2A-B), a finding consistent with the observation that overexpression of 7TMRs is not a common occurrence in human disease. GPR30 expression did not correlate with PR in primary tumors from patients with invasive ductal tumors. In contrast, a general pattern of agreement was observed between GPR30 and ER expression as nearly twice as many ER+ breast tumors coexpressed GPR30 relative to ER+tumors that failed to produce GPR30 (FIGS. 2A-B, Table II). However, approximately, 50% of ER− breast tumors retained GPR30, indicating that their expression is not interdependent (Table II). These finding demonstrate that tumors that maintain GPR30 but lack ER may remain estrogen responsive. PR expression was more than twice as common in tumors that coexpressed ER and GPR30 compared with breast tumors that produced ER but not GPR30 (72% versus 28%, respectively, Table III). This observation is interesting in that PR expression has been used as a rational approach for refining the identification of breast tumors suitable for treatment by ER antagonism. This rational is predicated on the fact that the PR genes, PR A and PR B, encode estrogen response elements (EREs) that interact with liganded ER to promote estrogen-dependent gene transcription. GPR30 expression may further predict ER functionality, and subsequent PR transcription, by virtue of the fact that ER gene transactivation is augmented by extracellular-regulated kinases, Erk-1 and Erk-2, which are activated by GPR30-dependent EGFR transactivation. Although it is important to note that while Erk-dependent ER activation is measured in heterologous cells, it does not occur in breast cancer cells. However, it is also noteworthy that GPR30 is a Gs-coupled 7TMR capable of stimulating adenylyl cyclase and that cAMP has a negative regulatory influence on the EGFR-to-Erk signaling axis in breast cancer cells.

Via ER and GPR30, estrogen promotes signaling mechanisms whose effects are measured with distinctive kinetic patterns, suggesting that they function independently. Evidence of their autonomy is provided further by the fact that their expression in breast tumors is not interdependent (Table II). The data also support that mechanism that GPR30 and ER promote distinct biological responses (Tables IV and V). The most notable distinction is that GPR30 and ER independently predict the development of metastatic disease. Primary breast tumors expressing GPR30 are almost twice as likely to result in metastasis as compared to GPR30-negative primary tumors (OR 1.9, p-value=0.014). No significant association was found between ER expression and the presence of metastatic disease (p value=0.11). On the other hand, GPR30 demonstrates a diametrically opposed relationship with HER-2/neu; its expression varies directly with HER-2neu (Table IV), which is consistent with the capacity of GPR30 to transactivate EGF-related receptors through release of HB-EGF from breast cancer cells.

As discussed above, tumor size and invasion of axillary lymph nodes by breast tumor cells have been the most important pathological parameters that predict the occurrence of distant metastases. Primary tumors $\geq 2$ cm, ($T_2$), are associated with a greater risk for developing metastatic disease and this is also reflected in an increase in the prevalence of lymph nodes containing invading tumor cells. While GPR30 was found to significantly associate with tumor size in a direct manner, the likelihood of the relationship between GPR30 expression and lymph node invasion was lower. A trend of significance was observed (p=0.06; table IV), when GPR30 scores applying the standard binary scoring system reported by separating samples that are GPR30-negative (0, +1) from GPR30-positive (+2, +3). This trend improved slightly (p-value=0.04), when GPR30 expression was stratified by its raw score (0, +1, +2, +3, +4). Similarly, when grouping these variables in categories using best cutoff values, a marginally significant positive association was noticed between GPR30 and lymph node invasion, with a tendency for GPR30 positive primary tumors to affect invasion into 2 or more lymph nodes (p=0.06, OR=1.83). GPR30 was found to be associated with nodal invasion, and GPR30 was a clear predictor of distant metastases. Its expression in primary breast cancer strongly predicted the development of frank metastases (p=0.014, OR=1.9) (Table IV). The relationship between HER-2/neu and nodal invasion is controversial. While some reports show a direct association between HER-2/neu and nodal invasion, other studies have shown no link between these variables. In the NCI data set studies here, a significant relationship was measured between HER-2/neu and metastasis (p<0.01). GPR30-dependent tumors can disseminate by a mechanism that does not involve lymph node trafficking and adhesion. GPR30 promotes intracellular signals through its ability to transactivate EGFRs, and EGFR stimulation has been linked to increased tumor cell survival, growth, and invasion into the surrounding and/or distant tissues.

GPR30 plays a significant role in the progression of human breast cancer and is a useful and reliable diagnostic and prognostic tool upon which therapeutic intervention is based. These data demonstrate that GPR30 expression varies directly with HER-2/neu, and therefore are consistent with GPR30's role as an alternate estrogen receptor that facilitates both ER-dependent and EGFR-dependent action. GPR30 levels reliably identify individuals that are at risk of developing metastatic disease, a variable that most clearly reflects breast tumor progression and influences the therapeutic decisions in these patients.

Activation of GPR30, at the Plasma Membrane

GPR30 is associated with rapid estrogen-dependent, G-protein signaling and specific estrogen binding. The subcellular site of GPR30 action has heretofore been unclear. Prior studies employing antibodies and fluorochrome-labeled estradiol have failed to detect GPR30 on the cell surface suggesting that GPR30 may function uniquely among 7TMRs as an intracellular receptor. The data described below shows that detectable expression of GPR30 on the surface of transfected HEK-293 cells is selected by fluorescence-activated cell sorting. Expression of GPR30 on the cell surface was confirmed by confocal microscopy using the lectin, concanavalin A, as a plasma membrane marker. Stimulation of GPR30-expressing HEK-293 cells with 17β-estradiol (17β-E2) caused sequestration of GPR30 from the cell surface and resulted in its co-distribution with clathrin and mobilization of intracellular calcium stores. Evidence that GPR30 signals from the cell surface was obtained from experiments demonstrating that the cell impermeable estradiol-protein conjugates, E2-bovine serum albumin and E2-horseradishperoxidase, promote GPR30-dependent elevation of intracellular cAMP concentrations. Subcellular fractionation studies further support the plasma membrane as a site of GPR30 action with specific [$^3$H]-17β-E2 binding and G-protein activation associated with plasma membrane but not microsomal, or other fractions, prepared from HEK293 or SKBR3 breast cancer cells. These results indicate that GPR30, like other 7TMRs, functions as a plasma membrane receptor and promotes rapid estrogen signaling.

The following reagents and methods were used to elucidate subcellular location of GPR30 activity.

Cell Culture

Human SKBR3 breast cancer cells and HEK293 embryonal kidney cells were obtained from the American Tissue Culture Collection (Manassas, Va.) and cultured in phenol red-free (PRF) DMEM/Ham's F-12 medium supplemented with 10% fetal bovine serum as described previously.

Construction of HA-GPR30 Protein and Generation of Stable HEK-293 Transfectants Expressing Surface HA-GPR30

A hemagluttinin (HA)-epitope tag was incorporated at the amino terminus of human GPR30 by PCR stitching using molecular clone GPR-BR as template. For this purpose, a polymerase chain reaction (PCR) product encoding full length GPR30 protein was synthesized using forward (5'CACCG<u>AATTC</u>AGAGACATGTACCCATACGACGT-CCCAGACTACGCGGATGTGACTTCCCAAGCC 3'; SEQ ID NO:5) and reverse (5'CAAGGCTG<u>TCTAGA</u>CGG-CACTGCTGAACCT 3'; SEQ ID NO:6) oligonucleotide primers containing Eco RI and Xba I restriction sites, respectively (underlined). The nucleotide sequence encoding the HA epitope YPYDVPDYA nonamer, is shown in bold. The amplified product was cleaved with Eco RI and Xba I, purified by agarose gel electrophoresis and subcloned into pcDNA3.1Zeo (+) for expression (Invitrogen, La Jolla, Calif.). The resultant molecular clone, named HA-GPR30Zeo was transfected into HEK-293 cells using Lipofectamine (Invitrogen). Three days following transfection, 500 µg/ml Zeocin (Invitrogen) was added to the growth media. Two weeks later, more than 100 drug-resistant colonies were counted and all of the cells in these colonies were pooled together and propagated by cultivation in PRF-DMEM/F12 with 5% FBS in the absence of the drug. Immunofluorescence analysis with the HA antibody showed that a relatively small proportion of the cells displayed significant cell-surface expression of HA-GPR30. Therefore, transfected cells expressing HA-GPR30 on the cell surface were enriched from the Zeocin-resistant population by fluorescence-activated cell sorting using rabbit HA-specific polyclonal antibody. Transfectants were sorted based on their mean intensity fluorescence where the highest staining (upper one percentile) cells were gated under sterile conditions, expanded in culture, and then subjected to a second round of sorting. The resultant cell line, HEK-293 (HA-GPR30), was passed for several months in cell culture and remained cell surface-positive for GPR30. HEK-293 (HA-β$_1$AR) cells were generated in a similar manner by transfection and drug selection using HA-β1AR plasmid DNA. Flow cytometry-assisted selection was not necessary in order to establish detectable HA-β1AR on the surface of HEK-293 cells.

Antibodies

Rabbit anti-hemagglutinin (HA) epitope antibody and agarose beads conjugated with HA mAB, H7, were purchased from AbCam and Sigma, respectively. Goat Gαs subunit specific antibodies (sc-26766) were purchased from Santa Cruz Biotechnology. Affinity-purified rabbit GPR30 C-terminal peptide antibodies were previously described. Monospecific GPR30 antibody, 2F2, was generated in Balb/C mice that were immunized with synthetic peptide CAVIPDSTEQSD-VRFSSAV (SEQ ID NO:3) from the C-terminus of human GPR30 that was conjugated to Keyhole Limpet Hemocyanin using the bifunctional cross-linker, MBS, (n-Maleimidobenzoyl-N-hydroxysuccinimide ester). Mice were injected intraperitoneally at three-week intervals with GPR30 peptide-KLH conjugate mixed in Titer-max adjuvant (Sigma), and boostered intravenously with peptide three days prior to fusion. Spleens were then harvested, lymphocytes isolated and fused with mouse 8653 myeloma cells using polyethylene glycol and seeded into semi-solid containing selective media (hypoxanthine/aminopterin/thymidine) as described in the Clonal Cell-Hy Hybridoma Cloning Kit (Stem Cell Technologies). Supernatants from 952 resultant hybridomas were screened by ELISA for the presence of antibodies reactive to immobilized GPR30 C-terminal peptide. Hybridoma supernatants that were peptide reactive were rescreened for their capacity to immunoprecipitate recombinant GPR30 protein. Hybridomas positive by immunoprecipitation were subcloned in semi-solid media. GPR30 mAB 2F2 was purified from recloned culture supernatants by affinity peptide chromatography.

Flow Cytometry and Immunofluorescence

Adherent cultures of HEK-293 cells stably transfected with GPR30 or vector were detached in PBS supplemented with 0.5 mM EDTA and collected by centrifugation. The cell pellet was resuspended in ice-cold phenol-red free DMEM/F12 media, recentrifuged and washed in the same media for two additional cycles. Cells were then resuspended at $10^6$/ml and incubated with rabbit HA antibody (AbCam) or control rabbit IgG at 0.5 µg/ml for 1 h at 4 C. Cells were then washed free of primary antibody by three successive washes in ice-cold PRF-DMEM/F12 media and then exposed to Alexa-488 conjugated goat anti-rabbit IgG (Molecular Probes) at 2.5 µg/ml for 1 h at 4° C. Following this incubation period, cells were then washed three times in PRF-DMEM/F12 media and surface fluorescence was measured on $10^4$ cells using a FACSort analyzer (Becton Dickinson) with an Argon-ion 488 nm laser and CellQuest software.

To measure the surface expression of GPR30, HEK-293 cells stably transfected with (HA-GPR30) or (HA-β1AR) were plated in PRF-DMEM/F12 media on fibronectin-coated glass coverslips and then fixed in 4% paraformaldehyde-PBS. Cells were then reacted with rabbit anti-HA antibodies (Ab-CAM) or control rabbit immunoglobulin (0.5 µg/ml) for 30 min at 22° C. Following incubation in primary antibody, cells were washed 3 times in PBS and stained with Alexa 594-derivatized concanavalin A (100 µg/ml) and Alexa 488-derivatized anti-rabbit antibodies diluted at 1:800 for 30 min (Molecular Probes). Cells were then washed in PBS and mounted in Vectashield containing DAPI (Vector Laboratories). To measure trafficking of GPR30 from the cell surface, quiescent, adherent HEK-293 (HA-GPR30) cells were labelled with rabbit anti-HA antibodies, as above, and then stimulated with 17β-E2 (1 nM) for various lengths of time, and fixed in 4% paraformaldehyde. Fixed cells were treated for 60 s in 0.05% Triton X-100 in 50 mM Tris-HCl, pH 7.5, 150 mM NaCl and blocked in 5% BSA for 15 min. Permeabilized cells were exposed to anti-clathrin mouse mAB (ab2371; AbCam) (6 µg/ml) for 30 min, washed and stained with Alexa-488-anti-mouse and Alexa594-anti-rabbit antibodies for 30 min (each at 1:800). Excess antibody was removed by washing in PBS, and coverslips were mounted in Vectashield with DAPI. Cells were visualized using a Nikon E600 microscope equipped with epifluorescence.

Immunoprecipitation and Deglycosylation

HEK-293 cells stably transfected with HA-GPR30 or HA-β1AR were grown to confluence in 10-cm culture dishes, washed three times with ice-cold PBS, and lysed in RIPA-buffered detergent (50 mM Tris, pH 7.6, 1% Triton X-100; 1% deoxycholate, 0.1% sodium dodecyl sulfate, 150 mM NaCl, 50 mM NaF, 2 mM PMSF plus protease inhibitors (Complete TM). Total cell protein was determined by BCA. Total protein (1 mg) was cleared with protein G-agarose beads to minimize the interaction of nonspecific proteins with immunoabsorbent beads. Precleared cellular protein was incubated with 3 µg of GPR30 mAB 2F2 overnight and antigen-antibody complexes were collected with protein G agarose beads for 1 h at 4° C. Immunoabsorbed proteins were eluted with Laemmli sample buffer containing β-mercaptoethanol at ambient temperature, size-fractionated by SDS-PAGE, and electrotransferred to nitrocellulose. The filter was blocked with nonfat-dried milk (5%) prepared in TBS containing 0.05% Tween-20 (TBS-T) overnight. Eluted proteins were visualized by blotting with rabbit GPR30 peptide antibodies diluted 1:500 in TBS-T for 2 h at room temperature. Rabbit GPR30 antibodies were detected using secondary goat anti-rabbit horseradishperoxidase and ECL.

Deglycosylation of immunopurified HA-GPR30 protein was carried out with N-glycosidase F (PNGase F) or Endoglycosidase H (Endo H) according to the manufacturer's specifications (New England Biolabs). Sample incubation in the absence of enzyme was performed as a control. Reactions were stopped in Laemmli sample buffer containing β-mercaptoethanol.

Intracellular Calcium Mobilization and Measurement of cAMP

Cells were seeded in fibronectin-coated 8-well cover glass chambers (Nunc, Lab-tek II), serum-starved in PRF DMEM/F12 and then loaded with fluo-4 (Invitrogen) (5 µg/ml for 15 min). Cover glass chambers were placed in a microscope stage incubator (20/20 Technologies, Eugene, Oreg.) at 37° C., and imaged using a inverted scope (Nikon TE2000E), with a 20× Plan Apo objective and a cooled CCD camera (Roper CoolsnapHQ, Photometrics, Tucson, Ariz.). Images were collected every second for 10 minutes. Data was quantified and analyzed using Metavue Software (Molecular Devices, Sunnyvale, Calif.) and Microsoft Excel. Background was subtracted, and fluorescence expressed relative to starting values. To measure intracellular cAMP, HEK-293 transfectants were subcultured in 6-well plates to near confluence. Cells were then incubated in serum-free phenol red-free DMEM/F12 medium for 3-5 h and treated with charcoal-stripped E2-BSA or E2-HRP or water-soluble E2 for 10 min. Cells were then digested with 0.1 M HCl and cAMP concentrations were measured in cytosolic fraction samples using an EIA kit following the manufacturer's instructions (Cayman Chemical, Ann Arbor, Mich.).

Preparation of Subcellular Fractions

Cells were washed with PBS, scraped from the plates, suspended in Hepes buffer and centrifuged at 5,000×g for 5 min. The cell fraction was resuspended in Hepes buffer and homogenized, followed by sonication for 10 sec. The nuclear fraction was obtained by centrifugation of the cell homogenate at 900×g for 7 min. A crude plasma membrane fraction was obtained by centrifuging the supernatant at 20,000×g for 30 min. A 3,500×g spin for 10 min was used initially prior to the 20,000×g spin to remove the heavy mitochondrial fraction but this step was eliminated in subsequent experiments because it had no effect on the binding results. The plasma membrane fraction was further purified using a sucrose pad (1.2 M sucrose in Hepes buffer, centrifuge at 6900×g for 45 min) as described previously. Microsomal (pellet) and cytoplasmic (supernatant) fractions were obtained by centrifugation at 100,000×g for 1 h of the remaining supernatant after the 20,000×g spin. Subcellular fractions were stored at −80° C. for up to 2 days prior to analysis. Cytochrome C reductase (NADPH) activity, an enzyme marker of the endoplasmic reticulum, was measured in subcellular fractions using a spectrophometric assay (Sigma, kit CY0100).

Western Blot Analysis of Subcellular Fractions

Western blot analysis for subcellular fractions was performed as described previously. Subcellular fractions were mixed with the 5× reducing lane marker sample buffers (ImmunoPure®, Pierce) and incubated for 10 min at 22° C. Samples were electrophoresed and blotted according to standard procedures. Rabbit GPR30 peptide antibody was used at a dilution of 1:500 in an overnight incubation at 4° C. after blocking with 5% nonfat milk in TBST buffer for 1 h. The membrane was subsequently washed 3 times and then incubated for 1 h at room temperature with horseradishperoxidase conjugated goat anti-rabbit IgG (Pierce), and then treated with enhanced chemiluminescence substrate (SuperSignal, Pierce) and exposed on film (Amersham).

Estrogen Receptor Binding Assay

Specific [$^3$H] 17βE2 binding assays for the plasma membrane, microsomal and nuclear subcellular fractions were performed according to known procedures. Specific [$^3$H] 17β-E2 binding of each subcellular fraction was obtained by subtraction of nonspecific binding [mixture of 4 nM [$^3$H] 17β-E2, 1 µM of 17β-E2 and subcellular sample (~250 µg protein)] from total binding (same mixture but without 17β-E2) after removing unbound (free) ligand. Bound [$^3$H] 17β-E2 from membranous fractions was captured on GF/B glass filters (Whatman). The percent recovery of protein samples after filtration ranged from 61.0% (microsomes) to 91.7% (plasma membrane). Dextran-coated charcoal was used to separate bound from unbound [$^3$H] 17β-E2 in a soluble receptor assay in cytosolic fractions.

[$^{35}$S] GTPγS Binding Assay

[$^{35}$S] GTPγS binding to the subcellular fractions were assayed as follows. Subcellular samples (150~200 µg protein) were incubated with 10 µM GDP and 0.5 nm [$^{35}$S] GTPγS (~12,000 cpm, 1.0 Ci/mol) in 300 µl Tris buffer [100 nM, NaCl, 5 mM $MgCl_2$, 1 mM $CaCl_2$, 0.6 mM EDTA, 0.1% BSA, and 50 mM, Tris-HCl (pH 7.4)] at 25 C for 15 min in the presence of 100 nM of 17β-E2 or equal volume of alcohol as control (CTL). Nonspecific binding was determined by addition of 500 nM GTPγS to the mixture. At the end of the incubation period, 300 µl of stop solution (10 mM GDP/GTPγS in Tris buffer) was added to the reaction tube, 200 µl aliquots were filtered through GF/B glass fiber filters, followed by several washes with the same buffer and subsequent scintillation counting.

Co-Immunoprecipitation of Gαs Subunit Protein with GPR30

SKBR3 cells were incubated with 100 nM 17β-E2 or no treatment (controls) for 20 min, followed by 2 washes with buffer. Plasma membrane and microsomal fractions were prepared as described above and incubated overnight at 4° C. with 1:200 of goat anti Gαs-subunit protein antibody (Santa Cruz Biotechnology, Inc., Santa Cruz, Calif.). The fractions were subsequently incubated for 2 h at 4° C. with protein-A agarose beads (Santa Cruz). The beads were washed several times and the immunoprecipitates were eluted by boiling for 10 min in SDS sample buffer. The solubilized immunoprecipitates were run on a 10% Tris-glycine SDS-polyacrylamide gel, the proteins were transferred to nitrocellulose membranes, and the membranes were blocked, incubated overnight with GPR30 antibody (1:500) and visualized.

GPR30 is Expressed on the Cell Surface and Promotes Intracellular Signaling

Figure 4:
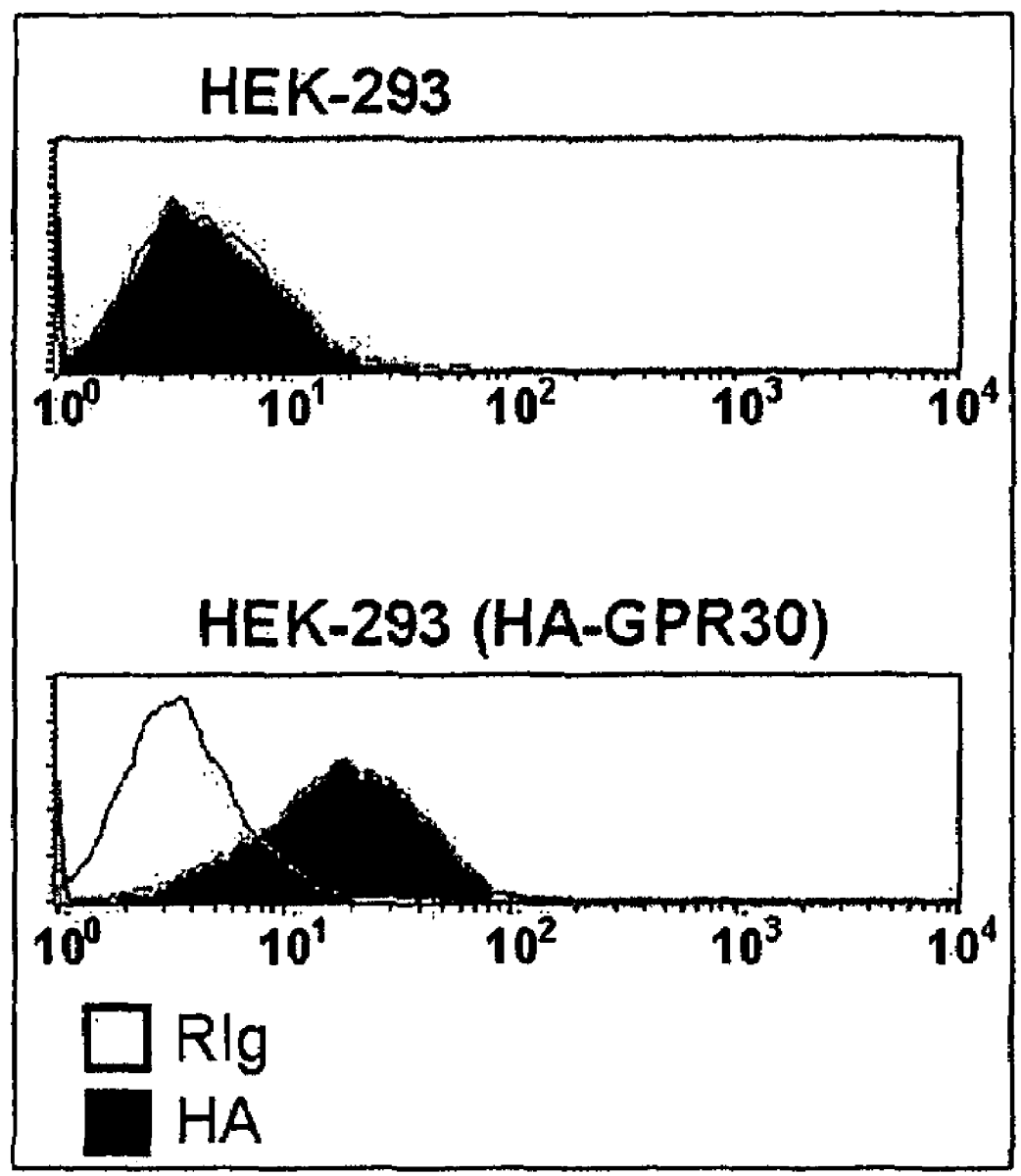
FIG. 4. is a histogram showing expression of GPR30 on the cell surface by flow cytometry. Histograms were generated from flow cytometry analysis of HEK293 cell lines stably expressing HA-tagged GPR30 or vector. Cells were stained with rabbit anti-HA antibody (HA, black) or control IgG (Rig, white). The x-axis values are displayed on a logarithmic scale as arbitrary fluorescence units and the y-axis values are plotted on a linear scale as number of cells.

7TMRs are type-I, N-linked glycoproteins, whose amino terminus faces the extracellular environment. To address whether GPR30 protein can be detected on the cell surface by cytofluoresence, recombinant GPR30 protein was engineered containing a hemagluttinin (HA) epitope tag on its amino terminus and expressed in HEK-293 cells. Following transfection and drug selection, the expression of GPR30 on the surface of intact HEK-293 (HA-GPR30) cells was evaluated by flow cytometry using HA antibodies following enrichment by fluorescence-activated cell sorting. The HA-enriched HEK-293 (HA-GPR30) cells exhibited an average relative mean intensity fluorescence (MIF) that was 8-10 fold greater than HEK-293 control cells indicating that HA-GPR30 is expressed on the cell surface (FIG. 4).

Figure 5A:
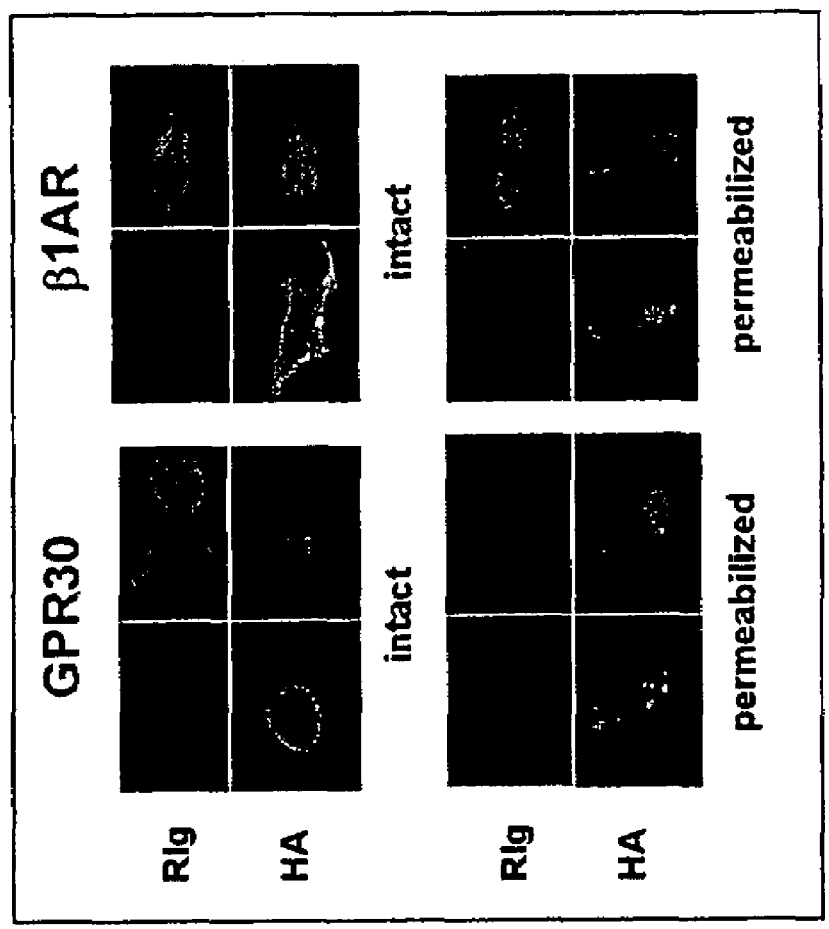
FIG. 5A is a series of photographs showing epifluorescent images of paraformaldehyde-fixed, intact (above) or Triton X-100-permeabilized (below), HEK-293 cells expressing HA-GPR30 or HA-β1AR cells were immunostained with rabbit HA antibodies or rabbit control immunoglobulin (Rlg). Cell-associated antibodies were detected using Alexa 488-derivatized anti-rabbit antibodies. Nuclei are stained using DAPI (blue).
Figure 5B:
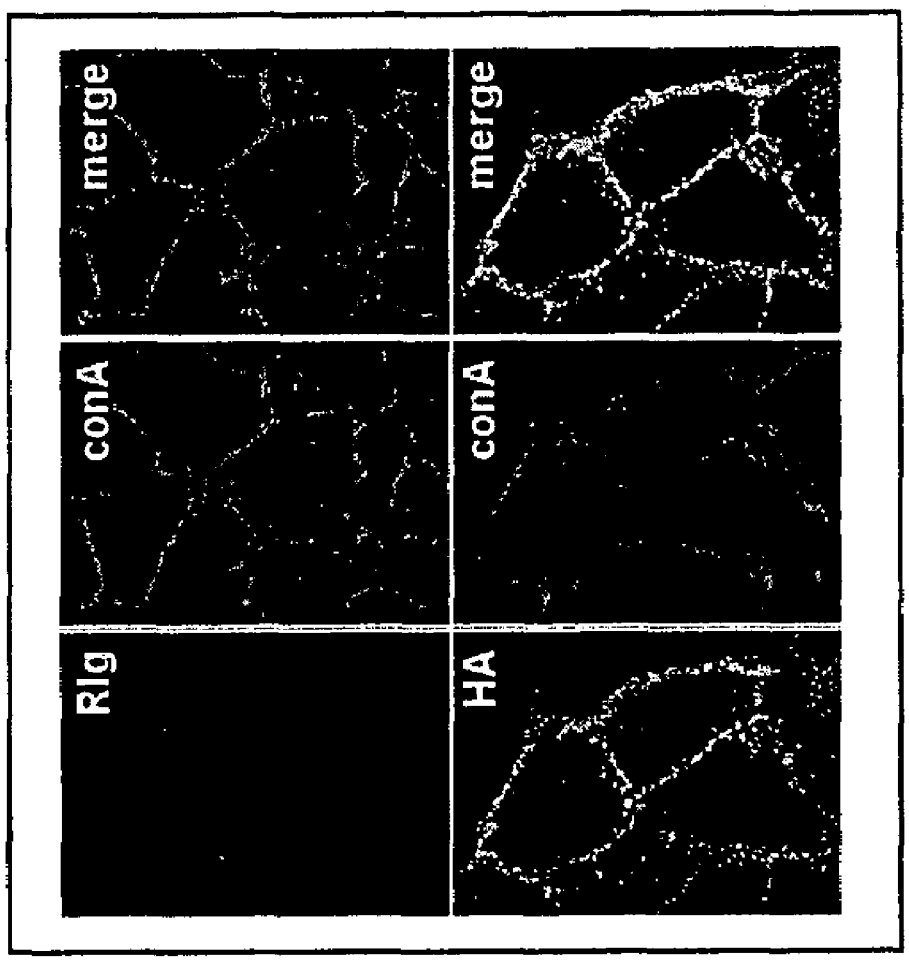
FIG. 5B is a series of photographs showing confocal microscopy images of paraformaldehyde-fixed HEK-293 (HA-GPR30) cells co-stained with Alexa-594-labelled concanavalin A, which specifically binds α-mannosyl saccharides in plasma membrane glycoproteins, and GPR30 peptide or control rabbit antibodies. Co-localization of GPR30 with con A is observed in the merge (yellow). These data demonstrate the subcellular localization of GPR30.

Epifluorescent images collected from HA-GPR30 and HA-$\beta_1$AR cells immunostained with rabbit HA antibodies clearly demonstrate that HA is concentrated at the cell surface (FIG. 5A), albeit the surface expression of HA-$\beta$1AR was slightly higher than that of HA-GPR30. Specific HA immunostaining of submembranous vesicles was observed upon permeabilization of either cell type with Triton X-100. No immunoreactivity was observed in either HEK-293 transfectant (intact or permeabilized) that was stained with rabbit control IgG. Localization of HA-GPR30 within the plasma membrane was confirmed by confocal microscopy using Alexa 594-labelled concanavalin A, a lectin which specifically binds to α-mannosyl saccharides expressed in the core structures of plasma membrane glycoproteins, as a plasma membrane marker (FIG. 5B). A circumferential staining pattern was observed in serial Z-section stacks prepared from paraformaldehyde-fixed HA-GPR30 cells that were stained with Alexa 594-conjugated concanavalin A (red) (FIG. 5B). HA rabbit antibodies, which were detected with Alexa 488-conjugated secondary antibodies, showed a similar cell surface-staining pattern compiled from these optical sections (green). Co-expression of HA-GPR30 and con A is clearly observed when the HA- and con A-stained sections are registered (yellow) (FIG. 5B). In contrast, control rabbit immunoglobulin showed no appreciable reactivity, and reactivity was not detected in cells that were co-stained with control antibodies and con A. These immunofluorescent data strongly suggest that the HA epitope of the HA-GPR30 protein is expressed on the cell surface.

Figure 6:
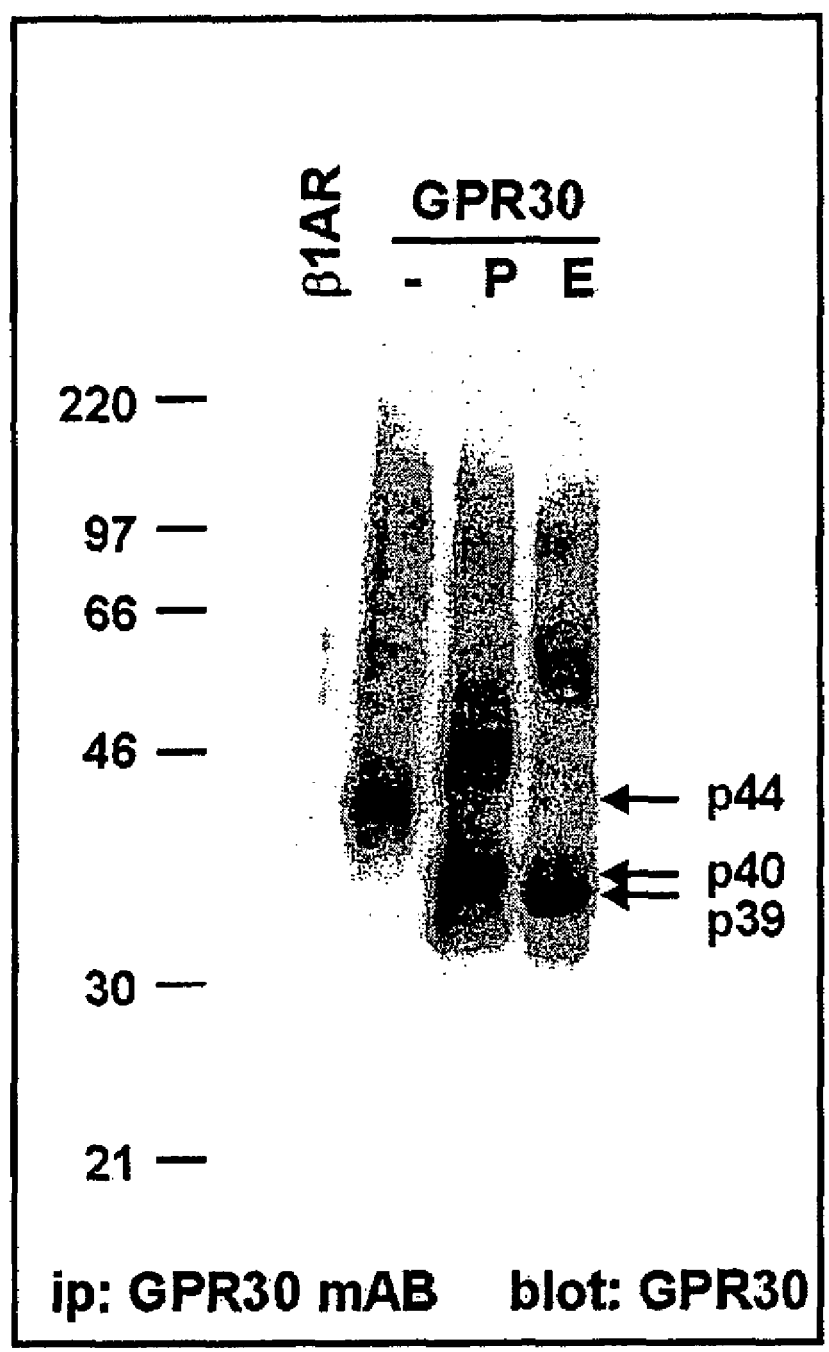
FIG. 6 is a photograph of an electrophoretic gel showing cellular expression of HA-GPR30 protein. Detergent lysates (0.5 mg) from HEK-293 (GPR30) cells or HEK-293 (β1AR) control cells were immunoprecipitated with mouse GPR30 mAB, 2F2. Immunoprecipitated protein was left untreated (−) or deglycosylated by incubation with PNGase F (P) or Endoglycosidase H (E). Samples were subsequently resolved by 10% SDS-PAGE and blotted with affinity-purified rabbit GPR30 antibodies. Gels shown are representative of three independent experiments.

Cellular expression of HA-GPR30, and its relative content of N-linked glycan side chains were assessed by comparing the relative mobilities on SDS-polyacrylamide gels of immunopurified GPR30 proteins that were untreated or treated with glycosidases (FIG. 6). GPR30 immunoprecipitates were prepared from HEK-293 (HA-GPR30) and control HEK-293 ($\beta$1AR) cells using monoclonal GPR30 peptide antibody, 2F2. Immunoprecipitated proteins were eluted, and analyzed by immunoblotting with rabbit GPR30 antibodies. The predominant protein species specifically detected by the GPR30 antibody, possessed an apparent molecular mass of 44 kDa, although other species with larger apparent molecular masses were also detected. Removal of N-glycan chains by treatment with N-glycosidase F (PNGase F) or Endoglycosidase H (Endo H) resulted in the appearance of major bands with molecular masses of 40 kDa and 39 kDa, respectively, which closely approximates the predicted molecular mass of the unmodified GPR30 core protein fused to the HA-epitope tag.

Figure 7A:
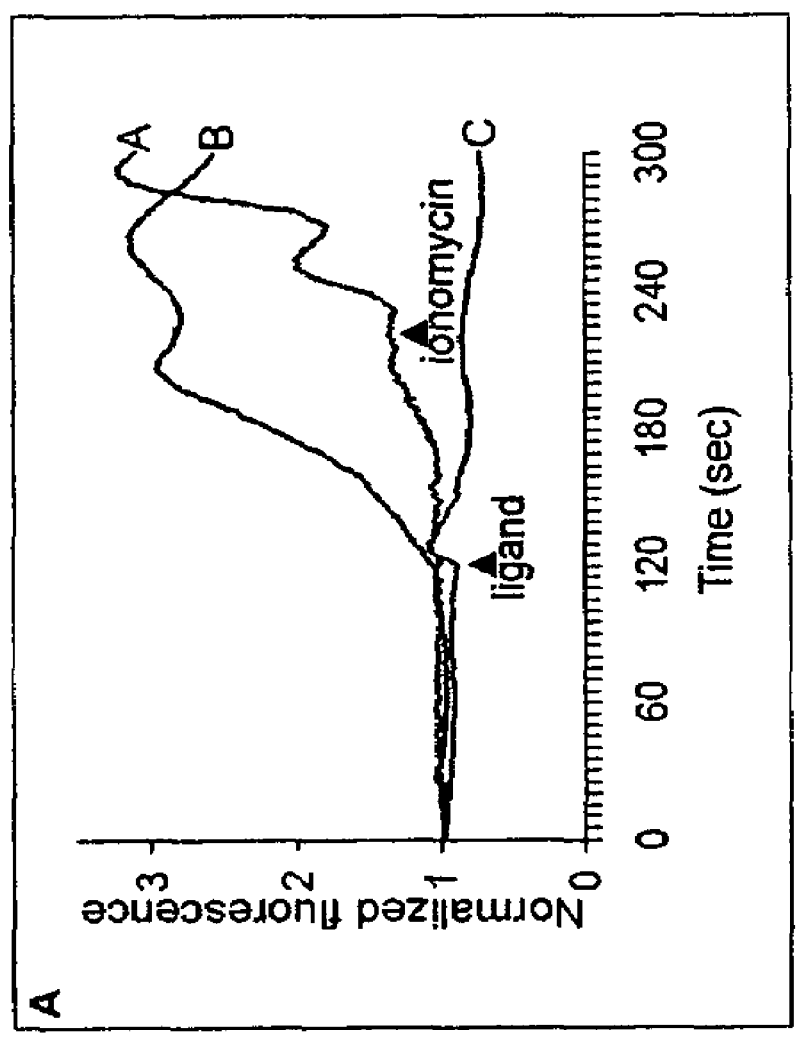
FIG. 7A is a line graph showing that 17β-E2 promotes GPR30-dependent release of intracellular calcium. Fura-loaded HEK-293 (vector) cells (A) or HEK-293 (HA-GPR30) cells (B,C) were stimulated with 10 nM of 17β-E2 (A,B) or 17β-E2 (C) at 120 s. Calcium ionophore was added at 220 s in (A).
Figure 7B:
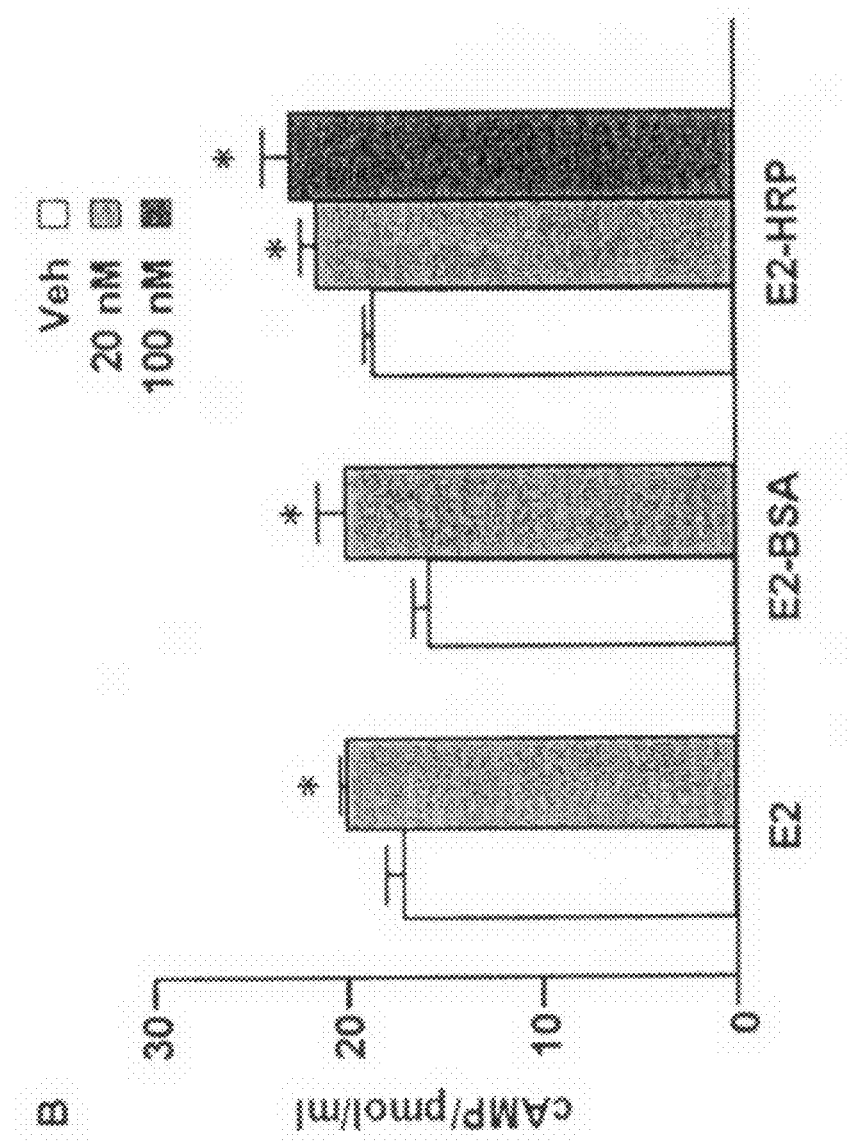
FIG. 7B is a bar graph showing results from HEK-293 (HA-GPR30) cells that were exposed to the indicated concentrations of charcoal-stripped E2-horseradishperoxidase (E2-HRP) or E2-bovine serum albumin (E2-BSA) or water-soluble 17β-E2 or control vehicle (Veh) for 10 min. Intracellular cAMP was measured by ELISA. The experiments shown represent three separate experiments. *, $P<0.05$ relative to the control treatment group. The data indicate that HA-GPR30 promotes intracellular signaling following stimulation with 17β-estradiol or membrane-impermeable 17-estradiol conjugates.

Addition of the HA-tag to GPR30 did not compromise receptor functionality as assessed in two independent analyses. First, the ability of 17$\beta$-E2 to stimulate the release of intracellular calcium was determined (FIG. 7A). Vector-transfected HEK-293 cells did not release calcium fluorochrome in response to 17$\beta$-E2 but remained sensitive to calcium ionophore (tracing A). In contrast, GPR30-expressing cells released stored calcium following treatment with 10 nM 17$\beta$-E2 (tracing B), but not with 17$\alpha$-E2 (tracing C). This response was rapid with peak levels (~3-fold increase) measured within 60 sec, indicating HA-GPR30 functions to trigger estradiol-mediated intracellular signaling. Secondly, GPR30 couples to Gas-protein and activates adenylyl cyclase in response to E2 stimulation. To determine whether GPR30 acts at the cell surface to promote estrogen-dependent intracellular signaling, intracellular cAMP concentrations were measured in HEK-293 (HA-GPR30) cells after stimulation with cell-impermeable estradiol conjugates (FIG. 7B). Mean basal intracellular cAMP concentrations of 18.5 pmoles were measured in quiescent cells. Exposure to 20 nM 17$\beta$-E2 for 10 min resulted in a significant increase in intracellular cAMP (22.0 pmoles). Similar increases in intracellular cAMP were observed following short-term exposure to the same concentrations of charcoal-stripped E2-BSA or E2-HRP (22.0 and 24.0 pmoles, respectively). These results indicate that functional HA-GPR30 is expressed upon the cell surface and promotes rapid E2 signaling as measured by stimulation of adenylyl cyclase and release of intracellular calcium.

Figure 8:
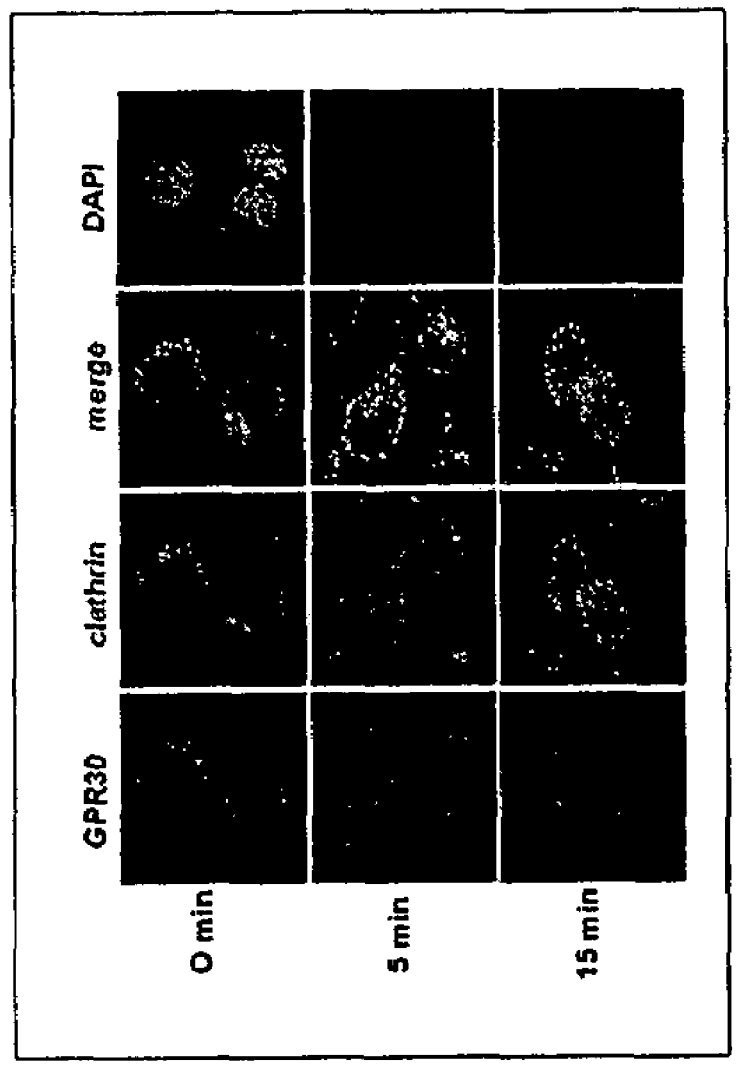
FIG. 8 is a series of photographs showing co-distribution of GPR30 and clathrin following 17β-estradiol stimulation. HEK-293 (HA-GPR30) cells were prelabelled with rabbit HA antibody. After removing excess antibody, cells were left untreated or stimulated with 17β-E2 (1 nM; 0, 5 or 15 min) and then fixed in paraformaldehyde. Cells were then permeabilized and incubated with mouse clathrin antibody. Cell-associated antibodies were detected using Alexa 594-conjugated anti-rabbit antibodies and Alexa 488-conjugated anti-mouse antibodies (green). Co-distribution is demonstrated in the merge. Nuclei are detected by DAPI.

Sequestration and Trafficking of GPR30 from the Plasma Membrane Following Estradiol Stimulation 7TMRs are sequestered from the cell surface and redistributed to clathrin-coated pits following ligand stimulation. To measure the trafficking of HA-GPR30 from the cell surface and to determine its distribution pattern with clathrin, immunofluorescent analyses were conducted on adherent cells that were prelabelled with HA antibody prior to estradiol stimulation (FIG. 8). Antibody-labelled, adherent cells were treated with 17$\beta$-E2, fixed and permeabilized with Triton X-100 and immunostained with clathrin-specific antibodies (FIG. 8). Co-distribution of GPR30 with clathrin was observed within 5 min of hormone treatment. By 15 min GPR30 was co-expressed with clathrin in a punctate staining pattern that was even more pronounced, with little GPR30 associated with the cell periphery, suggesting that 17$\beta$-E2 stimulation resulted in its redistribution to clathrin-coated vesicles. Clathrin co-distribution with GPR30 was not observed in cells stimulated with the control, 17$\alpha$-E2 (data not shown). These data indicate that GPR30 traffics from the plasma membrane, and enters clathrin-coated pits, following 17$\beta$-E2 stimulation.

Figure 9:
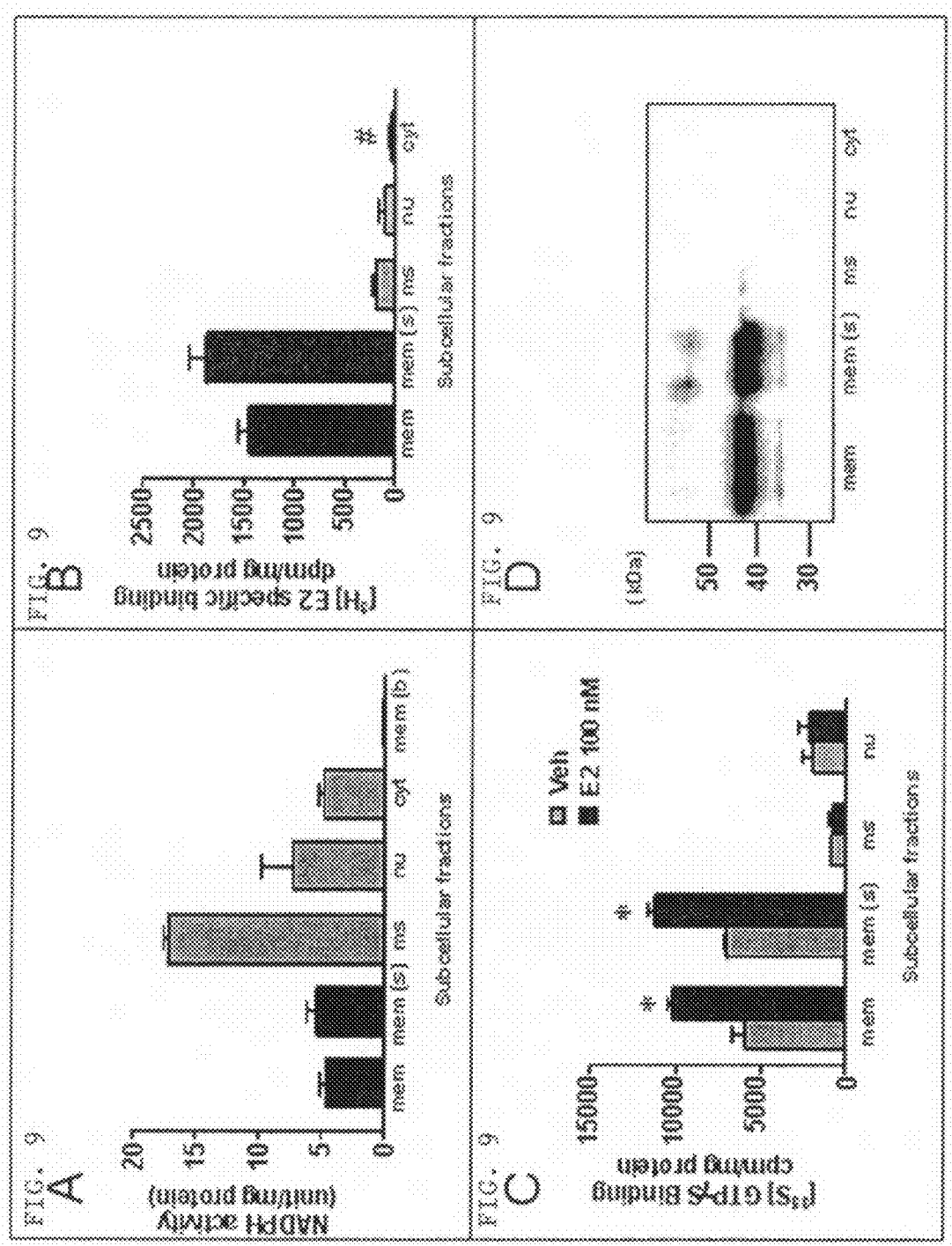
FIGS. 9A-C are bar graphs and FIG. 9D is a photograph of an electrophoretic gel showing the binding characteristics of subcellular fractions from HEK-293 (HA-GPR30) cells.

Estrogen Binding and G-Protein Activation are Associated with Plasma Membrane Fractions By radioreceptor assay, membrane fractions expressing GPR30 protein show specific estrogen binding and 17$\beta$-E2 dependent G protein activation. To examine the ability of other subcellular fractions to support GPR30-dependent estrogen binding and G protein activation, enriched plasma membrane, microsomal, nuclear and cytoplasmic fractions were prepared from HEK-293 (HA-GPR30) cells. As shown in FIG. 9A, NADPH oxidase was greatly enriched in microsomal fractions relative to all other subcellular fractions, which had similar low residual levels of enzyme activity in the spectrophotometric assay, indicating that the endoplasmic reticulum was largely absent from the non-microsomal fractions. Both crude and partially purified plasma membrane fractions displayed high specific [$^3$H] 17$\beta$-E2 binding activity (FIG. 9B), 6-8 fold higher than that in any other subcellular fractions on a mg/protein basis. Estrogen treatment caused G protein activation in the plasma membrane fractions as shown by a ~50% increase in specific [$^{35}$S] GTP$\gamma$S binding activity, whereas no activation of this signal transduction pathway was detected in microsomes or other subcellular fractions (FIG. 9C). These binding activities were positively associated with the expression of GPR30 protein (FIG. 9D), indicating that functional estrogen receptors were associated with enriched plasma membrane fractions that had the highest concentrations of GPR30 protein.

Figure 10:
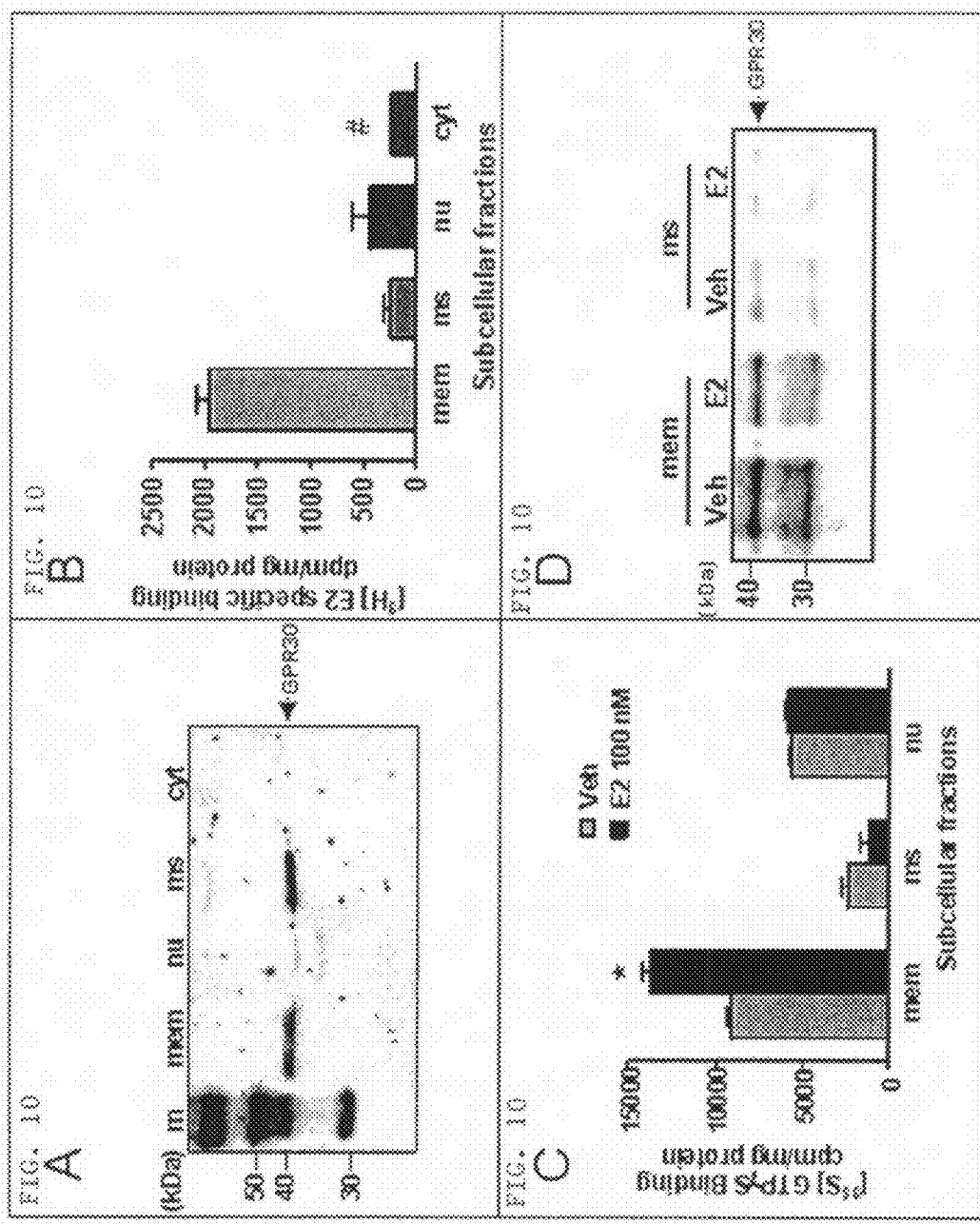
FIG. 10 D shows co-association of Gαs subunit protein with GPR30 in plasma membrane or microsomal fractions that were treated with 100 nM 17β-E2 or vehicle. Following treatment, G□s protein was immunoprecipitated from 500 μg of protein from each fraction using G□s-specific antibody. Associated GPR30 protein was detected by immunoblotting with rabbit GPR30 peptide antibodies. Molecular weight standards are designated at left. Location of GPR30 protein is denoted at right. N=2.

Expression of endogenous GPR30 protein in SKBR3 breast cancer cells is associated with estrogen binding. Therefore, the distribution of endogenous GPR30 protein and estrogen receptors was also assessed in subcellular fractions prepared from SKBR3 cells by Western blotting, radioreceptor assay, and GTP binding (FIG. 10A-D). Western blotting analysis demonstrated that while GPR30 protein is detectable within plasma membrane fractions, a significant portion of GPR30 protein is retained within the microsomal fractions (FIG. 10A). However, 17β-E2 binding activity (FIG. 10B) and estrogen-enhanced GTP binding (FIG. 10C) is not readily measurable within the microsomal fractions, or other intracellular fractions, but instead is concentrated within the plasma membrane fraction. This finding is consistent with a model of 7TMR activation supporting the coupling of GTP with the Gα subunit dissociated from ligand-occupied receptors. To directly test this concept, the association of Gαs protein with GPR30 in various cellular fractions was measured (FIG. 10D). More GPR30 was found coupled to Gs in plasma membrane fractions than in microsomal fractions, a finding consistent with the concentration of Gs protein within the plasma membrane. 17βE2 treatment triggered Gαs uncoupling from GPR30 indicating G protein activation (FIG. 10D). The data indicate that high affinity 7TMRs coupled to Gα subunit proteins accumulate in the plasma membrane. Subsequent to ligand binding and Gα protein release, they assume a conformation associated with low affinity for ligand, and are transported to intracellular vesicles for 7TMR recycling or receptor degradation in late endosomes.

Location and Mechanisms of GPR30 Activation

Estrogen has long been known to trigger rapid biochemical signaling events, including activation of second messenger cascades and lipid/protein kinases. Similarly, other steroid hormones and their antihormones also elicit rapid actions. While some debate exists regarding the receptor(s) that promote these effects, the rate by which these actions occur is consistent with the plasma membrane as a site of origin for these signaling events, a mechanism that is supported by the fact that both heterotrimeric G-proteins and EGFRs play a role in rapid estrogen action. GPR30 regulates adenylyl cyclase and also triggers extracellular release of proHB-EGF through the activation of membrane-tethered matrix metalloproteinases. Thus, GPR30 promotes its actions through two plasma membrane-associated enzymes. Yet, studies with fluorescently-labelled estradiol conjugates as well as green fluorescent protein-GPR30 fusion proteins have shown that GPR30 accumulates in the endoplasmic reticulum, and perhaps in other tubuloreticular compartments, and in intracellular vesicles, but could not be detected in the plasma membrane. This result was interpreted to suggest that GPR30 may function intracellularly even though this subcellular site is inconsistent with the known mechanisms by which 7TMRs promote cell signaling. Prior to the data described herein, there was some confusion regarding the receptor mechanism by which estrogen promotes rapid signaling.

Here, evidence is provided that GPR30, like all other members of the 7TMR superfamily, is a plasma membrane receptor. Estrogen binding and G-protein activation was found to be strongly associated with plasma membrane fractions (FIGS. 9A-D, 10A-D). Moreover, the fact that GPR30 is detectable in the plasma membrane (FIGS. 4, 7A and B, 8), becomes sequestered from the cell surface and co-distributes into clathrin-coated vesicles (FIG. 8), is consistent with the characterization of 7TMRs as plasma membrane receptors. In light of the data presented herein that GPR30, a structurally distinct estrogen receptor belonging to the 7TMR family, promotes rapid 17βE2 actions from the plasma membrane, this receptor is distinguished from the known ERs, ERα and ERβ and is referred to as a 7™-ER.

Expression of recombinant GPR30 protein and subsequent selection with antibodies directed against an N-terminally located epitope tag allowed for facile detection of GPR30 on the cell surface by a cytofluorescent technique. The abundant expression of GPR30 within the intracellular compartment (FIGS. 5A,C) may be a product of receptor trafficking patterns observed for other 7TMRs. Retention of 7TMRs within the endoplasmic reticulum is a common feature of 7TMR biogenesis as a consequence of multiple regulatory events, including carbohydrate processing, disulfide bond exchange and proteolytic editing. Further complexity is provided by the fact specific chaperone proteins have been identified, e.g. DrIP and RAMPs, that allow for 7TMR export. Intracellular retention as a consequence of receptor endocytosis is a common fate for 7TMRs, and provides an explanation as to why 7TMRs concentrate intracellularly. For these reasons, concentrated plasma membrane expression of 7TMRs is not generally observed in nature, and perturbations in 7TMR function linked with human disease are the consequence of dysregulated receptor trafficking and activity. Localization of endogenous GPR30 in the plasma membrane of SKBR3 cells (FIG. 10A-D), indicates that this location cannot be easily dismissed as anomalous receptor distribution as a result of epitope tagging and overexpression of recombinant GPR30. Surface expression of endogenous GPR30 is further supported by the recently published immunoelectron microscopy data demonstrating that GPR30 concentrates within the plasma membrane of pyramidal neuronal cells of the rat hippocampus. However, the results do not exclude the possibility that GPR30 may signal from the endoplasmic reticulum, or other intracellular locations.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for predicting an increased risk of developing distant metastatic neoplastic disease in a subject diagnosed as comprising a primary tumor, said method comprising
   a) detecting a GPR30 level in a tissue sample obtained from said primary tumor,
   b) comparing the GPR30 level of said tumor sample to a control GPR30 level obtained from a normal tissue, wherein said GPR30 comprises amino acids 25-375 of the amino acid sequence of SEQ ID NO: 7, and wherein an increase in the GPR30 level of said tumor sample indicates that said subject is at an increased risk of developing a malignant tumor at an anatomical site distant from said primary tumor, thereby predicting an increased risk of developing distant metastatic neoplastic disease.

2. The method of claim 1, wherein said subject is further diagnosed as comprising lymph node metastasis.

3. The method of claim 1, wherein said subject is further diagnosed as not comprising lymph node metastasis.

4. A method for predicting an increased risk of developing one or more tumorous foci in breast tissue of a subject diagnosed as comprising a primary tumor, said method comprising
   a) detecting a GPR30 level in a tissue sample obtained from said primary tumor,
   b) comparing the GPR30 level of said tumor sample to control GPR30 level obtained from normal tissue,
   wherein said GPR30 comprises amino acids 25-375 of the amino acid sequence of SEQ ID NO: 7, and wherein an increase in the GPR30 level of said tumor sample indicates that said subject is at an increased risk of developing one or more tumorous foci in an ipsilateral or a contralateral breast relative to said primary tumor, thereby predicting an increased risk of developing one or more tumorous foci in breast tissue.

5. A method of prognosis for a breast cancer patient, comprising
   a) detecting a GPR30 level in a sample of breast tissue following excision of a primary tumor,
   b) comparing the GPR30 level of said breast tissue to a control GPR30 level obtained from normal breast tissue,
   wherein said GPR30 comprises amino acids 25-375 of the amino acid sequence of SEQ ID NO: 7, and wherein an elevation in the level of GPR30 in said breast sample indicates a recurrence of malignancy, thereby prognosing a beast cancer patient.

6. A method for predicting survival time of a cancer patient, comprising
   a) detecting a GPR30 level in a cancer tissue biopsy from said patient,
   b) comparing the GPR30 level of said biopsy sample to a control GPR30 level obtained from normal tissue,
   wherein said GPR30 comprises amino acids 25-375 of the amino acid sequence of SEQ ID NO: 7, and wherein an increase in GPR30 level in said biopsy sample correlates with a decrease in survival time, thereby predicting the survival time of said cancer patient.

7. The method of claim 1, wherein said detecting step comprises contacting said tissue sample with an antibody or fragment thereof.

8. The method of claim 7, wherein said antibody is a monoclonal antibody.

9. The method of claim 7, wherein said antibody is a polyclonal antibody.

10. The method of claim 7, wherein said antibody or fragment thereof binds to an epitope in an amino sequence of the C-terminus of GPR30.

11. The method of claim 10, wherein said amino acid sequence comprises SEQ ID NO:3.

12. The method of claim 7, wherein said antibody or fragment thereof binds to an epitope in an amino sequence of the Exodomain II of GPR30.

13. The method of claim 4, wherein said detecting step comprises contacting said tissue sample with an antibody or fragment thereof.

14. The method of claim 13 wherein said antibody is a monoclonal antibody.

15. The method of claim 13, wherein said antibody is a polyclonal antibody.

16. The method of claim 13, wherein said antibody or fragment thereof binds to an epitope in an amino sequence of the C-terminus of GPR30.

17. The method of claim 16, wherein said amino acid sequence comprises SEQ ID NO:3.

18. The method of claim 13, wherein said antibody or fragment thereof binds to an epitope in an amino sequence of the Exodomain II of GPR30.

19. The method of claim 6, wherein said detecting step comprises contacting said tissue sample with an antibody or fragment thereof.

20. The method of claim 19, wherein said antibody is a monoclonal antibody.

21. The method of claim 19, wherein said antibody is a polyclonal antibody.

22. The method of claim 19, wherein said antibody or fragment thereof binds to an epitope in an amino sequence of the C-terminus of GPR30.

23. The method of claim 22, wherein said amino acid sequence comprises SEQ ID NO:3.

24. The method of claim 19, wherein said antibody or fragment thereof binds to an epitope in an amino sequence of the Exodomain II of GPR30.

25. The method of claim 1 or 4, wherein said control tissue is obtained from said patient prior to obtaining said tumor sample.

26. The method of claim 5, wherein said control tissue is obtained from said patient prior to obtaining said breast sample.

27. The method of claim 6, wherein said control tissue is obtained from said patient prior to obtaining said biopsy sample.

* * * * *

SEQUENCE LISTING

<160> NUMBER OF SEQ ID NOS: 7

<210> SEQ ID NO 1
<211> LENGTH: 11
<212> TYPE: PRT

-continued

<213> ORGANISM: Homo sapiens

<400> SEQUENCE: 1

His Glu Arg Tyr Tyr Asp Ile Ala Val Leu Cys
1               5                   10

<210> SEQ ID NO 2
<211> LENGTH: 15
<212> TYPE: PRT
<213> ORGANISM: Homo sapiens

<400> SEQUENCE: 2

Lys Gln Ser Phe Arg His Ala His Pro Leu Thr Gly His Ile Cys
1               5                   10                  15

<210> SEQ ID NO 3
<211> LENGTH: 19
<212> TYPE: PRT
<213> ORGANISM: Homo sapiens

<400> SEQUENCE: 3

Cys Ala Val Ile Pro Asp Ser Thr Glu Gln Ser Asp Val Arg Phe Ser
1               5                   10                  15

Ser Ala Val

<210> SEQ ID NO 4
<211> LENGTH: 24
<212> TYPE: PRT
<213> ORGANISM: Homo sapiens

<400> SEQUENCE: 4

Met Asp Val Thr Ser Gln Ala Arg Gly Val Gly Leu Glu Met Tyr Pro
1               5                   10                  15

Gly Thr Ala Gln Pro Ala Ala Cys
            20

<210> SEQ ID NO 5
<211> LENGTH: 64
<212> TYPE: DNA
<213> ORGANISM: Homo sapiens

<400> SEQUENCE: 5
caccgaattc agagacatgt acccatacga cgtcccagac tacgcggatg tgacttccca      60
agcc                                                                  64

<210> SEQ ID NO 6
<211> LENGTH: 30
<212> TYPE: DNA
<213> ORGANISM: Homo sapiens

<400> SEQUENCE: 6
caaggctgtc tagacggcac tgctgaacct                                       30

<210> SEQ ID NO 7
<211> LENGTH: 375
<212> TYPE: PRT
<213> ORGANISM: Homo sapiens

<400> SEQUENCE: 7

Met Asp Val Thr Ser Gln Ala Arg Gly Val Gly Leu Glu Met Tyr Pro
1               5                   10                  15

Gly Thr Ala Gln Pro Ala Ala Pro Asn Thr Thr Ser Pro Glu Leu Asn

-continued

```
            20                  25                  30
Leu Ser His Pro Leu Leu Gly Thr Ala Leu Ala Asn Gly Thr Gly Glu
            35                  40                  45

Leu Ser Glu His Gln Gln Tyr Val Ile Gly Leu Phe Leu Ser Cys Leu
            50                  55                  60

Tyr Thr Ile Phe Leu Phe Pro Ile Gly Phe Val Gly Asn Ile Leu Ile
65                          70                  75                  80

Leu Val Val Asn Ile Ser Phe Arg Glu Lys Met Thr Ile Pro Asp Leu
                    85                  90                  95

Tyr Phe Ile Asn Leu Ala Val Ala Asp Leu Ile Leu Val Ala Asp Ser
                    100                 105                 110

Leu Ile Glu Val Phe Asn Leu His Glu Arg Tyr Tyr Asp Ile Ala Val
            115                 120                 125

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
            370                 375
```